(12) United States Patent
Blake, III et al.

(10) Patent No.: US 9,681,877 B2
(45) Date of Patent: Jun. 20, 2017

(54) SURGICAL CLIP APPLIER

(71) Applicants: Joseph W Blake, III, New Canaan, CT (US); Patrick N Gutelius, Monroe, CT (US); Jeffrey H MacDonald, Bantam, CT (US)

(72) Inventors: Joseph W Blake, III, New Canaan, CT (US); Patrick N Gutelius, Monroe, CT (US); Jeffrey H MacDonald, Bantam, CT (US)

( * ) Notice: Subject to any disclaimer, the term of this patent is extended or adjusted under 35 U.S.C. 154(b) by 752 days.

(21) Appl. No.: 13/987,017

(22) Filed: Jun. 25, 2013

(65) Prior Publication Data

US 2014/0379003 A1 Dec. 25, 2014

(51) Int. Cl.
*A61B 17/128* (2006.01)

(52) U.S. Cl.
CPC ........ *A61B 17/128* (2013.01); *A61B 17/1285* (2013.01)

(58) Field of Classification Search
CPC . A61B 17/0469; A61B 17/29; A61B 17/2909; A61B 2017/2912; A61B 2017/1925; A61B 2017/00367; A61B 2017/2845
USPC ................ 606/139–143; 227/175.1
See application file for complete search history.

(56) References Cited

U.S. PATENT DOCUMENTS

| 5,431,668 | A | * | 7/1995 | Burbank, III | ........ A61B 17/128 227/901 |
| 5,700,270 | A | * | 12/1997 | Peyser | ............... A61B 17/1285 606/142 |
| 6,423,079 | B1 | * | 7/2002 | Blake, III | .......... A61B 17/1285 606/143 |
| 7,211,092 | B2 | * | 5/2007 | Hughett | ............... A61B 17/068 606/142 |
| 2010/0137886 | A1 | * | 6/2010 | Zergiebel | ............. A61B 17/128 606/143 |
| 2011/0144665 | A1 | * | 6/2011 | Malkowski | ........ A61B 17/1285 606/143 |

* cited by examiner

*Primary Examiner* — Robert Lynch
*Assistant Examiner* — Socrates L Boutsikaris
(74) *Attorney, Agent, or Firm* — Patrick J. Walsh

(57) ABSTRACT

A clip applier of handle and cartridge for applying clips in surgical procedures with handle preferably a scissors type defined by a housing of shell members containing a cam operated linear translator actuated by handle levers, an anti-backup mechanism limiting handle lever movement to full pull and release strokes while preventing partial pull or release handle strokes, and with cartridge fitted with lockout mechanism to disable applier after last clip is used in surgery, with a puller bar lock to hold puller bar position in cartridge prior to assembly with handle, a detent spring mounted in cartridge cover member as part of clip handling mechanism, and a rapid-fire pawl as part of clip handling mechanism to prevent cartridge jamming when clips are applied in rapid succession.

14 Claims, 19 Drawing Sheets

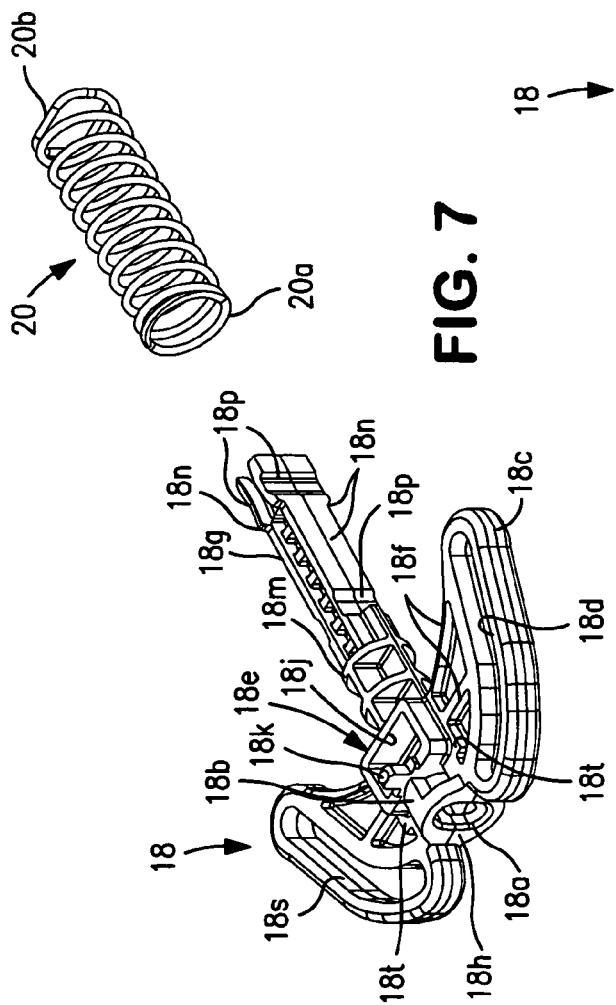
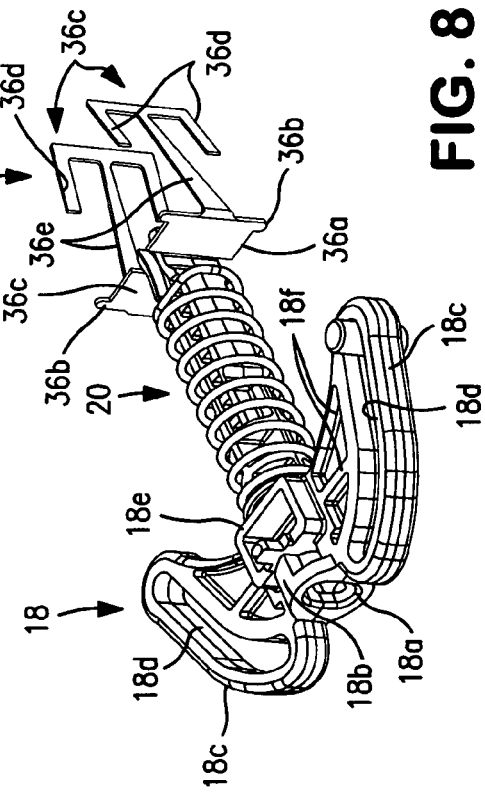
FIG. 7
FIG. 8

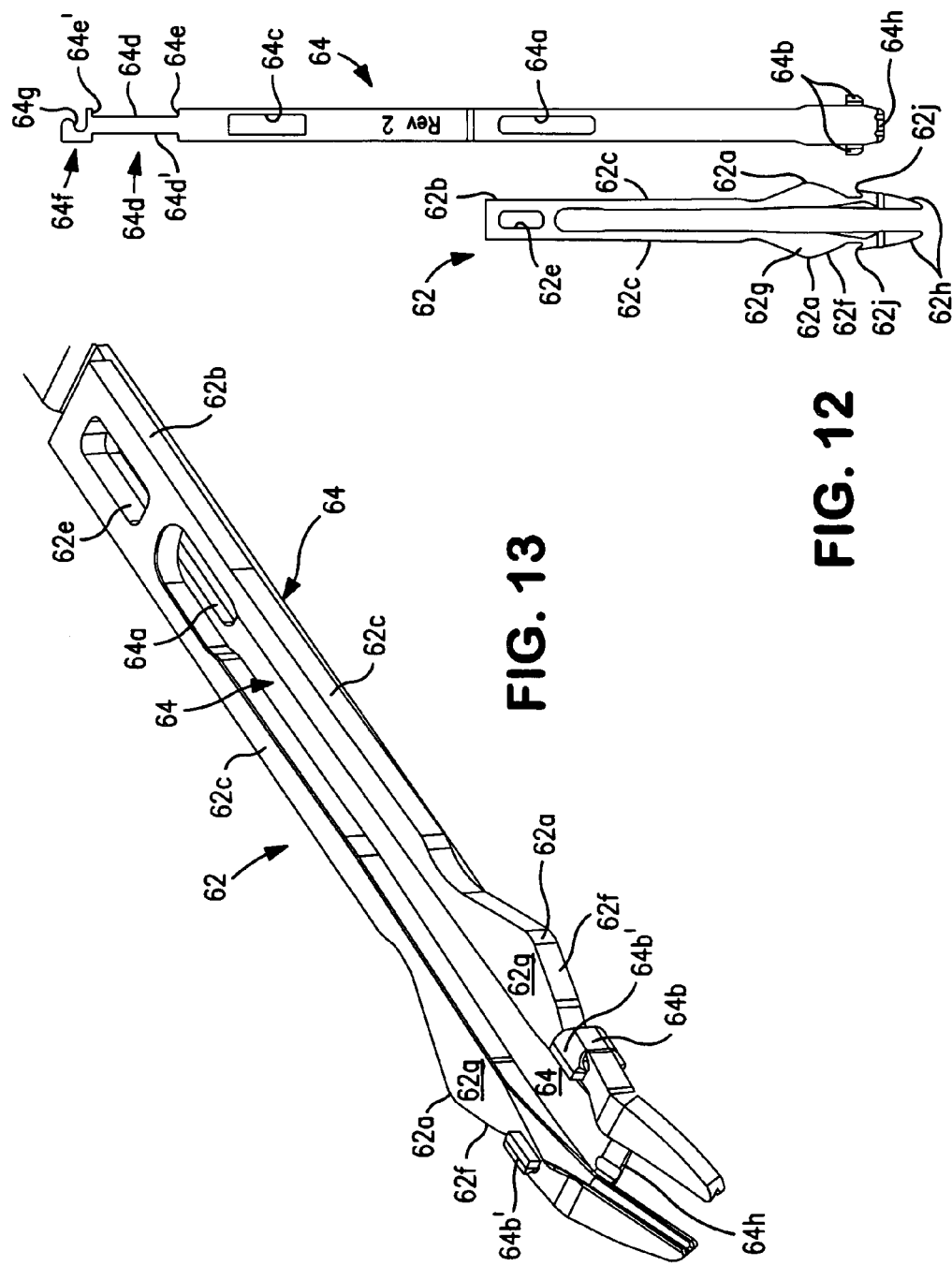

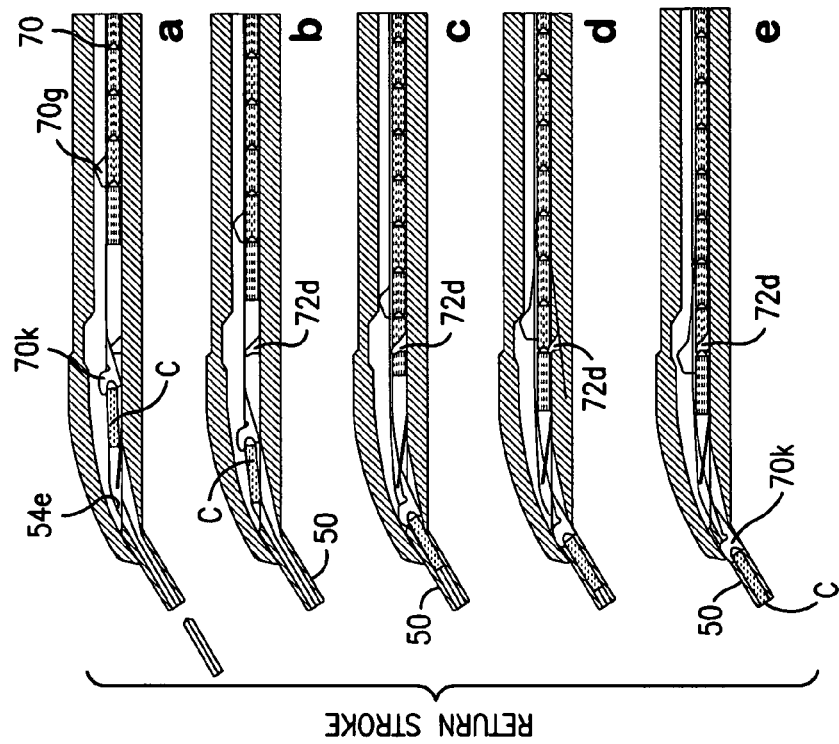
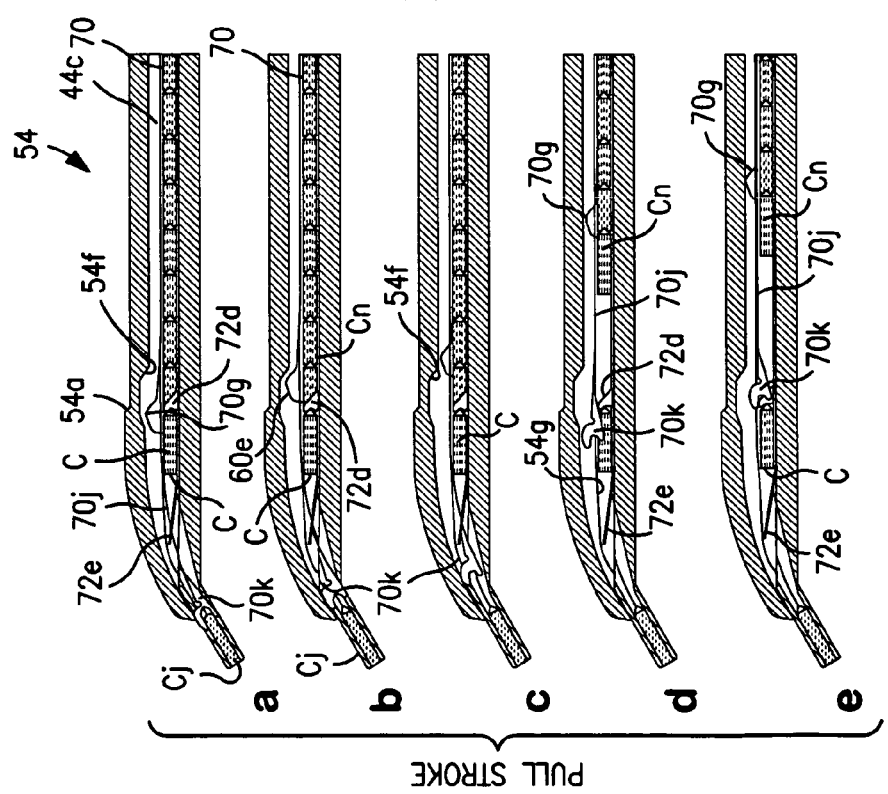

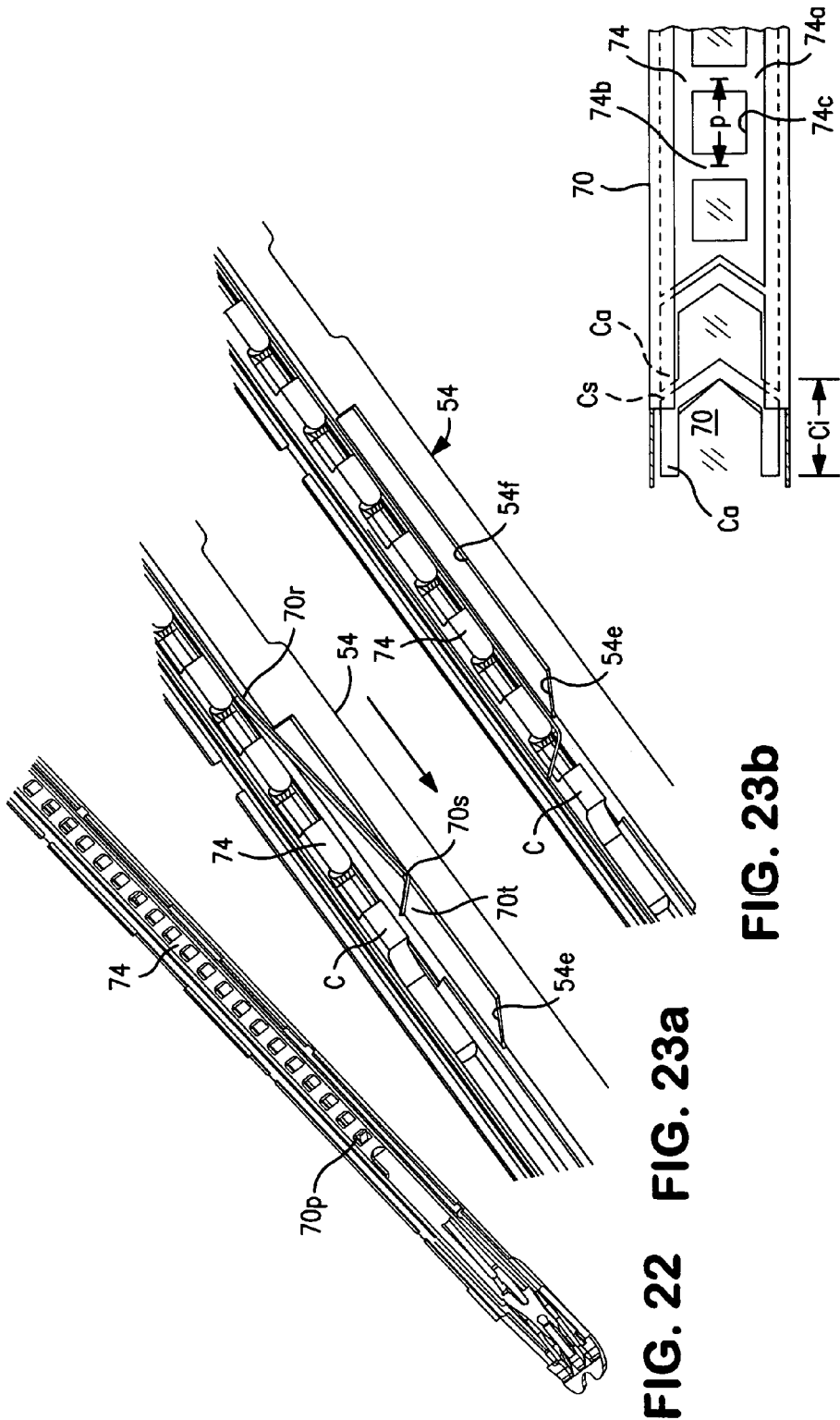

SURGICAL CLIP APPLIER

FIELD OF THE INVENTION

The present invention relates to surgical clip appliers as an instrument having a supply of clips for closing severed blood vessels and other fluid carrying ducts in surgical procedures.

BACKGROUND OF THE INVENTION

There are many different designs for surgical clip appliers for a variety of surgical procedures including both open and laparoscopic surgery.

This invention comprises improvements in repeating multi-clip appliers of the kind described and claimed in Joseph W Blake III U.S. Pat. Nos. 6,423,079 and 6,869,435, and in U.S. patent application Ser. No. 13/385,760 filed Mar. 6, 2012 entitled Surgical Clip Applier.

U.S. Pat. No. 6,423,079 describes a clip applier with an operating handle and clip applying mechanism performing an operating cycle in which a clip is applied in surgery and the clip applier jaws are reloaded with a single clip from a clip supply channel for clip application in the next cycle. The applier provides a moveable clip supply channel containing a line of clips that are released seriatim.

Clip crimping jaws apply a clip with a rearward movement of a cam member thereby allowing the functions of clip loading and jaw closure to be coordinated and operated by a single sliding bar moving reciprocally to load and fire clips. The clip actuating mechanism includes a combined actuating bar and in-line clip supply channel together with clip indexing mechanisms arranged so that with a squeeze of the operating levers, the actuating bar moves rearward in the appliance to apply a clip in surgery, capture the next in-line clip, index a line of clips rearward away from the clip jaws; and that with release of the operating levers, the jaws open, the next in-line clip is loaded into the jaws, the second next in-line clip is separated from the line, and the clip indexing movement is reset for the next cycle.

U.S. Pat. No. 6,869,435 discloses a repeating multi-clip applier having an operating handle housing cooperating with a removable and disposable clip applying cartridge. The operating handle housing comprises a pistol grip set of handles which provide linear reciprocating motion by means of a spring biased translator slide for actuating the clip applying mechanism within the cartridge. The operating handle housing includes a rotary forefinger wheel hub and rotatable drum subassembly which receive the clip cartridge for 360° rotation about the cartridge axis and which link the cartridge clip applying mechanism to the translator slide.

The operating handle housing further comprises an anti-backup mechanism to prevent a partial pull and release of the operating handles to avoid a well-known hazard that can occur when clip appliers are used in surgery. The hazard is that of dropping and losing a partially closed clip in a surgical site. The anti-backup mechanism avoids the hazard by preventing handle release before a clip in the instrument jaws is fully closed and applied at a surgical site.

The '435 clip applying mechanism includes a combined actuating bar and in-line clip supply cartridge together with clip advancing mechanisms arranged so that with a squeeze of the operating handle, the actuating bar moves rearward in the instrument to close its jaws to apply a clip in surgery, capture the next in-line clip, retain and move a line of clips rearward away from the clip jaws, and that with release of the operating levers, the jaws open, the next in-line clip is loaded into the jaws, the second next in-line clip is separated from the line, and the clip retaining means is reset for the next cycle.

U.S. patent application Ser. No. 13/385,760 filed Mar. 6, 2012 is directed to a surgical clip applier comprising handle and cartridge. The handle is a scissor type having a socket for receiving the cartridge and having levers and links for providing spring biased linear reciprocation motion to the cartridge. The handle further contains an anti-backup mechanism to ensure that handle movement is restricted to full pull and full release strokes. The cartridge has a pull bar for receiving linear reciprocating motion and for transmitting the motion to cartridge components for actuating clip applying jaws and components for supplying surgical clips one at a time to the jaws. For a squeeze and release of the handle, the clip applier applies a clip in surgery, separates the next clip from a stack of clips in a clip magazine, draws the remaining clip stack back from the jaws to keep stack together, draws a clip pusher into position behind the next clip, provides a safety toggle to ensure that jaws open to receive next clip, and advances next clip into the jaws. When the last remaining clip in the clip magazine is used, a lock out mechanism prevents further operation of handle and cartridge mechanisms.

In practice, clip cartridges are ordinarily used a single time and discarded. Operating handles, on the other hand, may be disposed of after use with a single cartridge, or may be used with a plurality of cartridges in a single surgical procedure and then discarded, or may be sterilized after each surgical procedure and used over and over again.

SUMMARY OF THE INVENTION

A preferred embodiment of repeating multi-clip applier according to the present invention comprises an instrument having an operating handle housing together with a removable and disposable clip applying cartridge. A full squeeze and release of operating handles applies a clip to a surgical site and reloads another clip into clip applying jaws of the instrument. The clip applier disclosed herein embodies improvements in handle and cartridge components with respect to the clip applier of the above-identified US patent application.

The operating handle housing of this invention preferably comprises a scissors grip handle which imparts linear reciprocating motion of fixed excursion to the clip applying mechanism within the cartridge. The fixed excursion is determined by a spring biased linear translator. The linear translator within the operating handle connects to an end of a puller bar of the clip cartridge mechanism wherein the puller bar receives and transmits linear reciprocating motion to operating components of the cartridge. The linear translator has a pair of cam channels connected by cam pins to scissor handle lever arms. As the handle lever arms are squeezed and released in operating the handle, the cam pins cooperate with cam channels to move linear translator through linear reciprocating motion of fixed excursion.

The operating handle housing accommodates an anti-backup mechanism to prevent handle release after a partial pull and also to prevent partial release after a full pull of the handles. As noted above, a partial pull and release of operating handles creates the hazard of the clip applier releasing and dropping a partially closed clip into a surgical site. Furthermore, partial release can result in double loading clips into crimping jaws, a condition that jams proper functioning of the applier mechanism. The anti-backup mechanism comprises cooperating springs with confronting spring tabs in fixed position within the handle housing for cooperation with anti-backup surfaces of the linear translator. When the scissor handles are actuated by squeezing them together, the anti-backup surfaces pass between the spring tabs preventing handle release until the spring tab edges enter an opening (marking one end-point of linear excursion) formed in the anti-backup surfaces. When in the opening, the spring tabs can toggle over so as to accommodate return excursion of the linear translator. The other end-point of return excursion is marked by another opening formed in the anti-backup surfaces, where linear translator is released for a return stroke.

A preferred embodiment of the cartridge comprises:
(i) a housing consisting of outer sleeve with chassis and cover providing a stationary base for operating cartridge members;
(ii) a puller bar as prime mover that receives from the operating handle and transmits to operating cartridge members a linear reciprocating motion of fixed excursion from which movement of individual cartridge members is derived;
(iii) a first set of cartridge members driven by the puller bar that actuate clip applying jaws for applying a clip in surgery;
(iv) a second set of cartridge members driven by the puller bar for handling surgical clips for the purpose of feeding the clips one at a time into the clip applying jaws;
(v) an arrangement of first and second set members cooperating in timed sequence such that in an operating cycle of the instrument during which the scissor handles undergo full pull and full release, a clip is applied in surgery and the next clip is advanced into the applier jaws;
(vi) a lockout mechanism that inhibits clip applier operation after the last remaining clip in a clip channel has been used in surgery; and,
(vii) a tissue stop for properly positioning clip and tissue at that moment when the clip is applied to tissue in surgery.

The clip applier has a novel mechanism with minimal complexity especially suited for a disposable cartridge for fixed handle appliances. The clip applier employs low operating force without recoil and is adaptable for use as a quick snap-in disposable cartridge with a fixed operating handle. The simplified mechanism reduces tooling and assembly requirements, provides high operating reliability at lower product cost.

Specific examples are included in the following description for purposes of clarity, but various details can be changed within the scope of the present invention.

OBJECTS OF THE INVENTION

An object of the invention is to provide a novel clip applicator with minimum complexity and with adaptability to a complete range of clip sizes used in open and laparoscopic surgery.

Another object of the invention is to provide a clip applicator adaptable for use with a replaceable cartridge.

Another object of the invention is to provide a clip applicator having an operating handle that provides anti-backup linear reciprocating motion.

Another object of the invention is to provide a clip applicator in which clip feed and applying mechanisms are driven by a translator having linear reciprocating motion generated by operating handles.

Another object of the invention is to provide a surgical clip applier with an anti-backup means to prevent release of partially closed clips at a surgical site.

Another object of the invention is to provide a surgical clip applier with an anti-backup means to prevent jamming of applier mechanism as a result of double loading of clips into clip crimping jaws.

Another object of the invention is to provide a clip applying cartridge which can be used with various operating handle configurations including pistol grip, scissor type, and surgical robot.

Other and further objects of the invention will become apparent with an understanding of the following detailed description of the invention or upon employment of the invention in practice.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIG. 7 is a perspective view of linear translator and handle main spring.

FIG. 8 is a perspective view of assembled anti-backup components comprising linear translator, handle main spring, and anti-backup springs.

FIG. 12 is a plan view of clip applying jaws and cam puller for actuating the jaws.

FIG. 13 is an enlarged perspective view of clip applying jaws and cam puller for actuating jaws.

FIGS. 19a-e are section views in elevation of front end of second set of cartridge members in a sequence of operational positions for pull stroke of clip applier handle.

FIGS. 20a-e are section views in elevation of front end of second set of cartridge members in a sequence of operational positions for return stroke of clip applier handle.

FIG. 22 is a fragmentary perspective view of assembled cartridge members of FIG. 21.

FIGS. 23a and 23b are fragmentary schematic views of operating positions of rapid fire pawl and ramp camming surface of FIGS. 21 and 22 with floor and clips removed for clarity.

FIG. 24 is a fragmentary plan view partly in section of clip magazine showing line of clips and pusher ladder.

DETAILED DESCRIPTION OF PREFERRED EMBODIMENT

Figure 1:
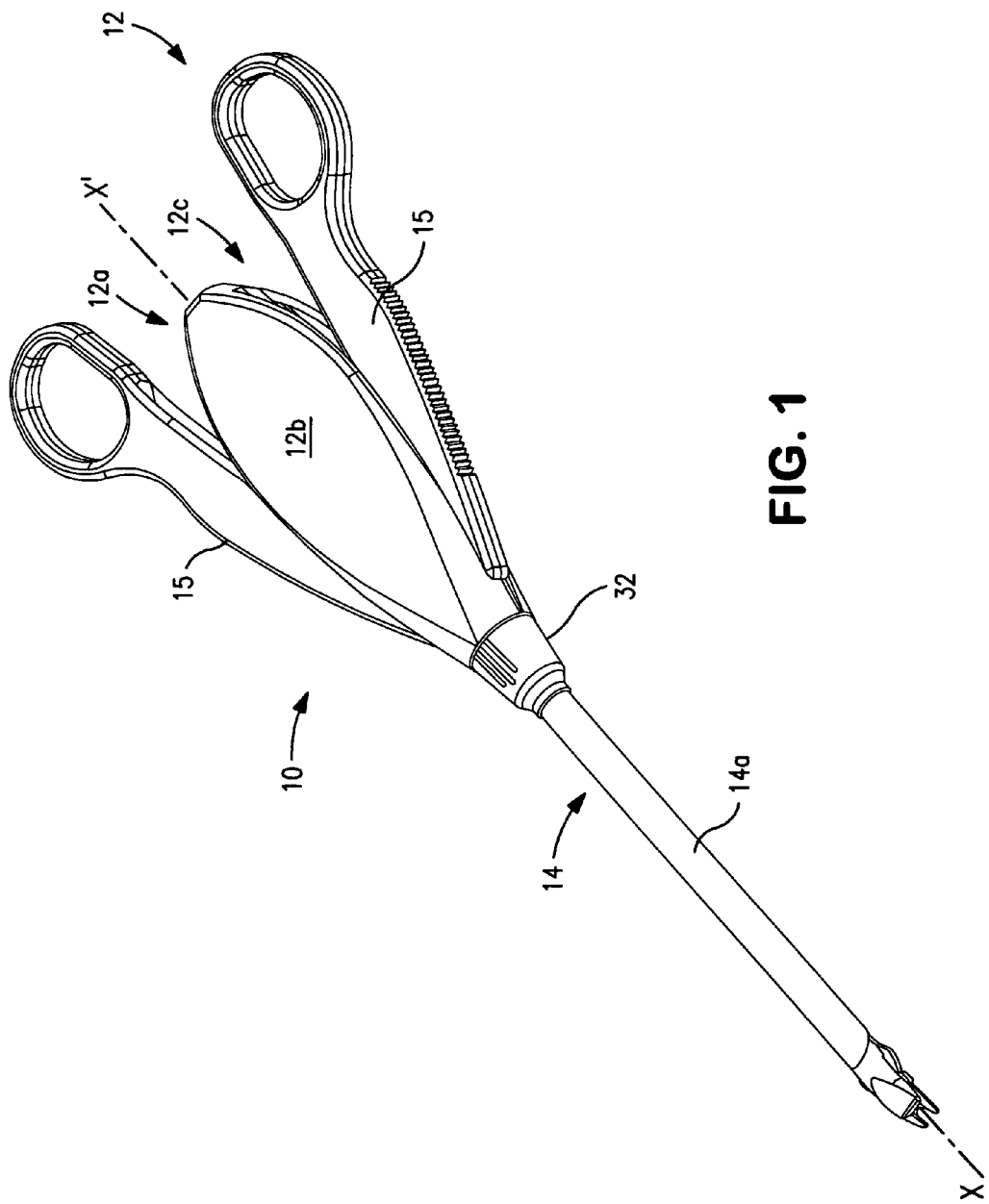
FIG. 1 is a perspective view of a preferred embodiment of surgical clip applicator comprising handle and cartridge.

Referring to the drawing, a preferred embodiment of the surgical clip applier 10 comprises operating handle 12 and clip applicator cartridge 14.

The operating handle 12 (FIGS. 1-2) is preferably scissors type with housing 12a of upper 12b and lower 12c housing shell members, scissor handles 15, cartridge socket 16, and an interior operating assembly of linear translator 18, scissor handle main spring 20, and anti-backup mechanism 22. Clip applicator cartridge 14 is inserted into the handle cartridge socket 16 for cooperation with handle interior assembly such that the handle provides the cartridge with linear reciprocating motion of fixed excursion controlled by anti-backup mechanism that restricts linear motion received by the cartridge to full close (pull) and full open (release) strokes. The handle main spring urges the linear translator, scissor handles, and clip applicator cartridge including clip applying jaws to open position. The cartridge when assembled to the handle is held against rotation about the cartridge axis as described more fully below.

Scissors handle comprises housing 12a of upper and lower shell members defining an interior space for positioning an interior assembly of linear translator 18, handle main spring 20, and anti-backup mechanism 22, and further defining cartridge socket 16 for receiving and holding cartridge 14. The upper and lower shell members provide pivot posts 12d for mounting handle lever arms 15.

FIGS. 2-6 illustrate interior configuration of lower shell member 12c which is identical to the interior configuration of upper shell member 12b. Lower shell member configuration shown best in FIGS. 4 and 5 comprises one-half each of the structure of pivot posts 12d, cartridge socket 16, transverse slot 16j, cage 24, linear translator box 26, transverse compartment 28, guide rail 30, segmented back wall 12e that are all brought to full structural formation when joined to identical upper shell member.

Longitudinally extending interior walls 12f provide side surfaces to define side openings 12g and marginal interior space 12h within the assembled housing shell for handle lever arms.

Shell posts 12d, 12j comprise complementary centering and receptor posts having the functions of (i) pivot posts 12d for lever arms in assembled handle, and (ii) assembly posts 12j for aligning and securing upper and lower shell members during manufacturing assembly of handle.

Multiple pairs of centering pins 12d', 12j' and receptor recesses 12d," 12j" (FIG. 4) serve an additional function as crush pins and sockets. The pins have cylindrical side walls that press fit into hexagonal receptor sockets so as to hold shell members together without need for sonic welding, glue, or fasteners.

Figure 4:
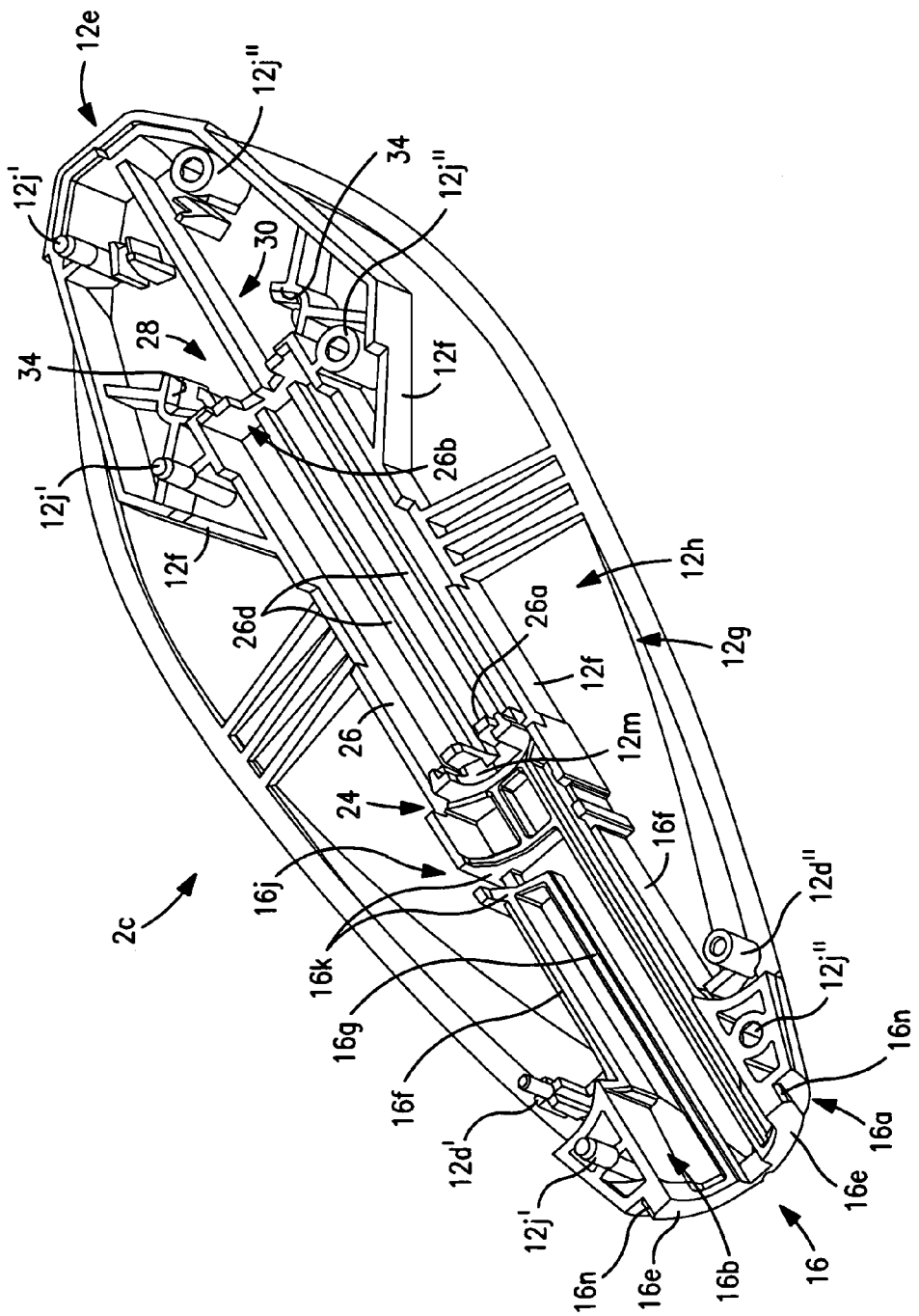
FIG. 4 is a perspective view of a cover shell showing its interior configuration.
Figure 5:
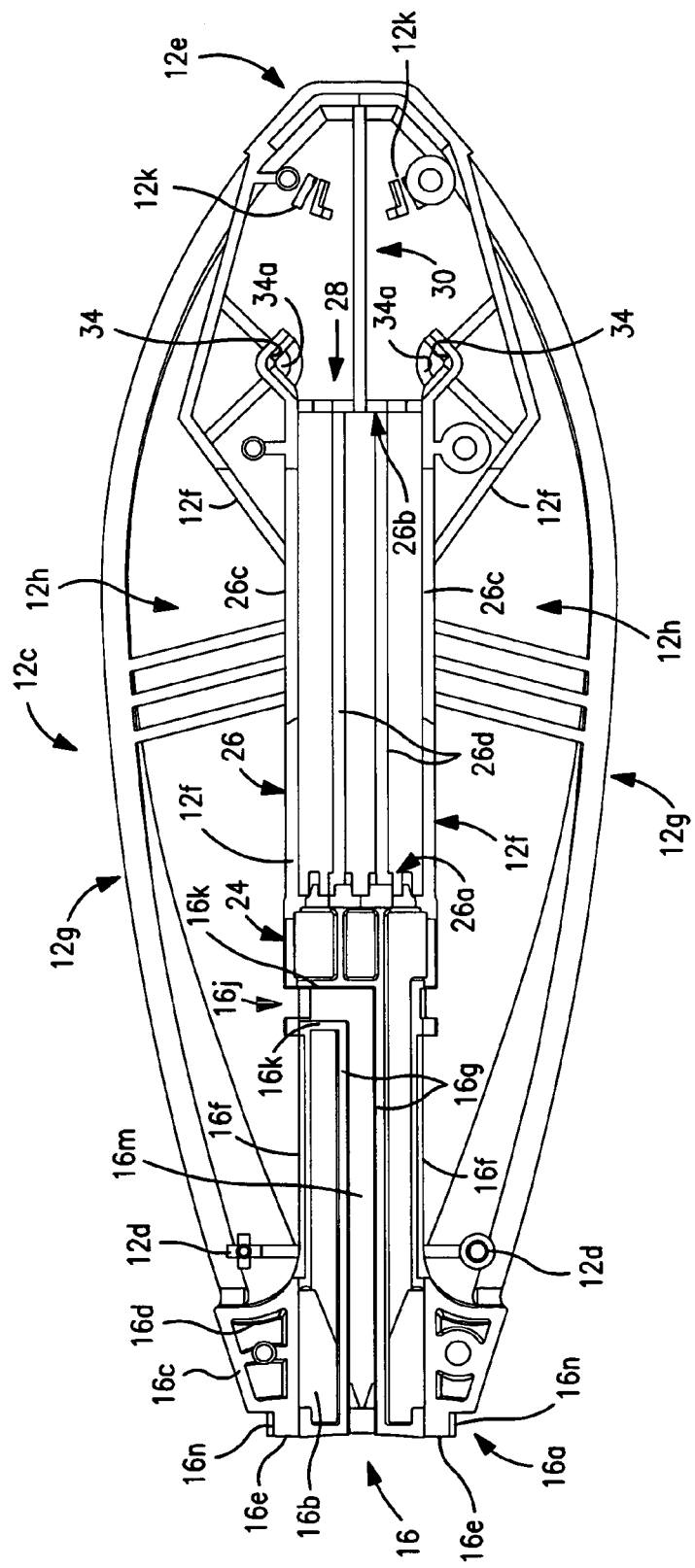
FIG. 5 is a plan view of the cover shell of FIG. 4.

As best shown in FIGS. 4 and 5, the housing upper and lower shells join to form cartridge socket opening 16 for insertion of cartridge into handle and an adjacent recess 16a for receiving the cartridge end cap 32. The socket opening is broadly defined by cylindrical interior wall 16b, frusto-conical outer wall 16c, by transverse support ribs 16d between these walls, and by front wall divided into recessed annular shoulder 16a and annular front face 16e.

The cartridge socket extends from cartridge opening at front end of the housing into the housing interior. Socket is defined by side panels 16f and by parallel guide ribs 16g defining an open ended channel for receiving and guiding clip applier cartridge into position in the handle. Guide ribs at their inner end terminate at transverse slot 16j situated between transverse walls 16k for receiving and retaining cartridge. The inner reach of the cartridge socket includes cage 24 (FIG. 6) defined by spaced side ribs 24a, circular inner ribs 24b, and by back wall 24c for receiving the end 32a (FIG. 14) of cartridge shaft cap 32 as its retaining lugs 32b enter socket transverse slots 16j.

The back wall 24c defines a front face stop for cartridge assembly and also a back face stop for limiting excursion of linear translator 18 in forward direction. In addition, the cartridge puller bar 40 T-shaped end 40a (FIG. 14) projects through back wall for connection with linear translator through aperture 18a (FIG. 7). At this connection, linear reciprocating motion is transmitted from handle to cartridge.

The upper and lower housing shell inner surfaces further define linear translator box 26 comprising front 26a and rear 26b walls, and side ribs 26c for positioning the linear translator 18 and handle main spring 20. Parallel axially extending rails 26d within the box support and center linear translator 18 and main spring 20 within the housing.

Handle main spring 20 (FIGS. 5-8) is coiled about the linear translator 18 and when assembled in linear translator box 26 is compressed against wall 26c as handle lever arms 15 are closed. Confronting V-shape recesses 34 behind the rear box wall 26c position spring of anti-backup spring 36 tabs 36a while anchor post 36b of each spring is retained in footing slots 34a. The upper and lower shells have cooperating anchoring footing slots 34a for retaining anchor post of anti-backup springs. The anti-backup springs 36 and linear translator 18 and associated housing fittings including linear translator box and V-shaped recesses, inter alia, form the anti-backup mechanism of the handle.

Figure 6:
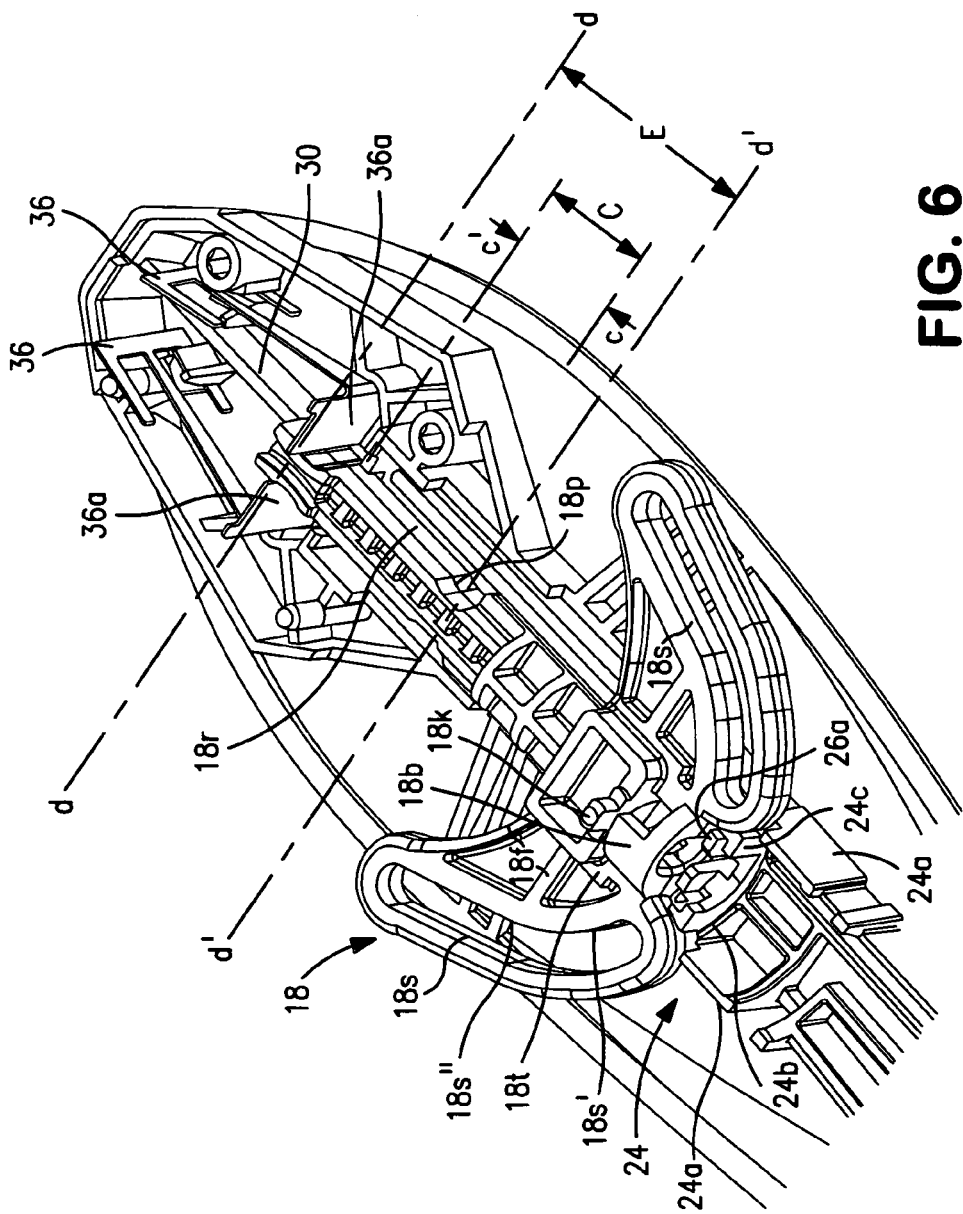
FIG. 6 is a perspective view of linear translator and antiback-up springs in position in bottom cover shell of handle.

FIGS. 5 and 6 show lower guide rail 30 and it is understood that upper shell provides upper guide rail extending between assembled anti-backup springs 36 for the purpose of guiding and constraining movement of the translator during handle actuation.

Figure 2:
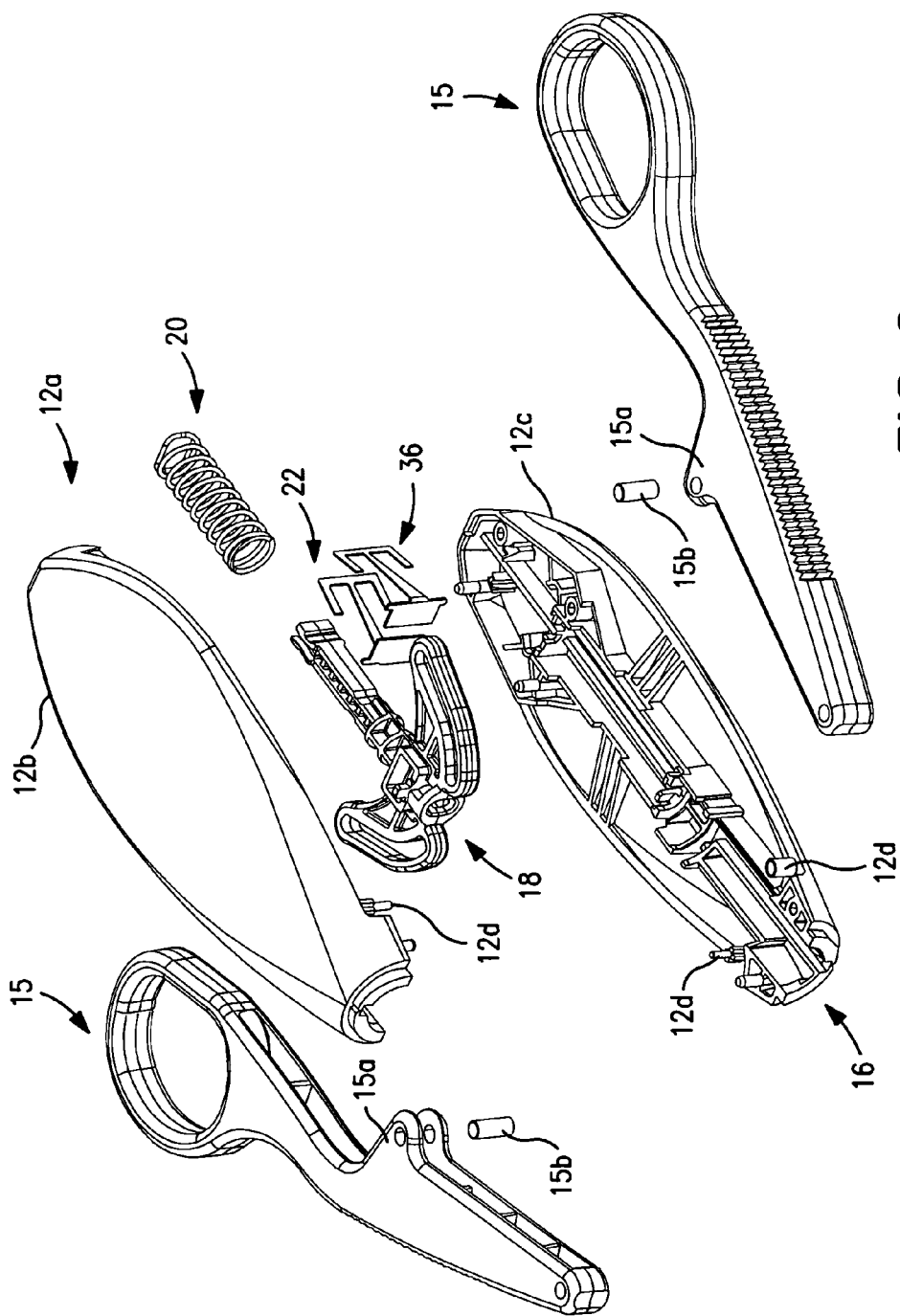
FIG. 2 is an exploded perspective view of preferred embodiment of all handle components.
Figure 3:
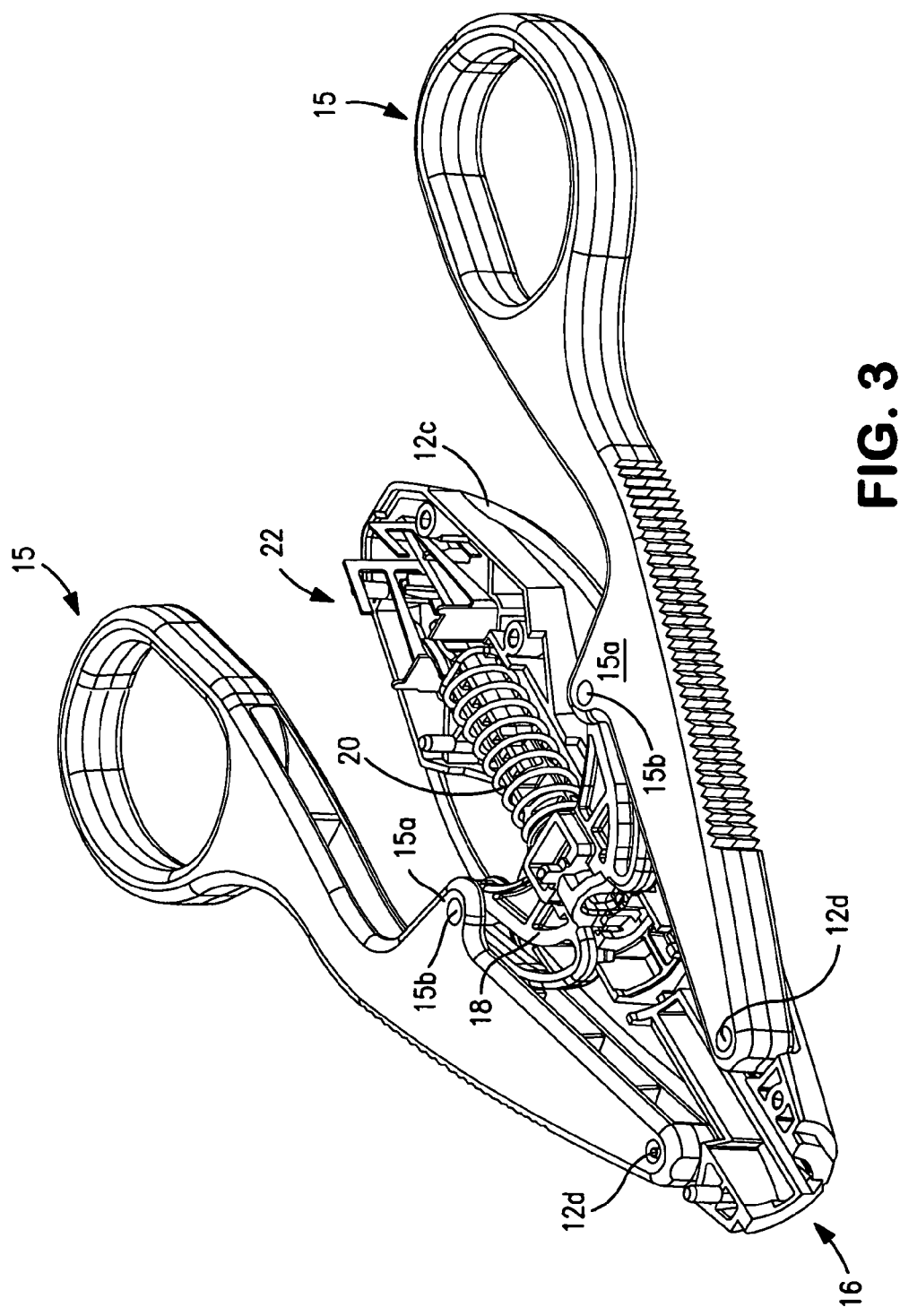
FIG. 3 is a perspective view of a preferred embodiment of surgical clip applicator handle with top cover shell of handle removed showing socket for cartridge, handle lever arms, subassembly of linear translator, handle main spring, and anti-backup mechanism.

As shown in FIGS. 1-3, handle lever arms 15 are nested in side openings of assembled shell housing, are mounted on pivot posts 12d for squeeze and release movement, have connecting wings 15a for transforming squeeze and release movement into linear reciprocating movement received by linear translator 18, are held in normal release position by main spring 20 urging linear translator to forward position, and have squeeze and release movement limited respectively by guide rails 30 and by face stop 26a that limits forward excursion of linear translator within linear translator box 26. In addition, squeeze and release movement of lever arms is further regulated by anti back-up mechanism described below in detail.

Referring to FIGS. 2, 3, 6, and 8, the handle includes linear translator 18 actuated by handle lever arms 15 for providing rectilinear motion of fixed excursion for operating clip applying components within the cartridge. The linear translator is a component of anti-backup mechanism that limits handle lever arm movement to full pull and release strokes for operating cartridge clip applying components, and is urged by handle main spring to normal position of released handle lever arms.

As best shown in FIGS. 3, 6, 7, and 8, linear translator 18 comprises cell 18b for receiving and retaining cartridge puller bar T-shaped end 40a through which linear motion is delivered to the cartridge; twin cam ovals 18c defining cam slots 18d through which handle lever arms move linear actuator rearward along handle A-A' axis; foundation block 18e for supporting cam ovals through struts 18f and for bearing force of handle main spring; and anti-backup beam 18g for positioning main spring, and cooperating with anti-backup springs 36 for limiting handle movement to full pull and release strokes.

Cell 18b is generally cylindrical with aperture 18a through front face 18h to admit T-end 40a of cartridge puller bar, and with inner space to retain T-end within the cell after the T-end (and cartridge) is rotated a quarter turn to complete the connection. Cell in forward position of the linear actuator (FIG. 6) abuts face of front wall 26a.

Foundation block 18e is defined by front, rear, and side wall members preferably in rectangular form to provide structural support through struts 18f for cam oval bodies 18c and to absorb camming forces delivered to cam oval bodies by handle lever arms. Rear wall of the block engages front end 20a of handle main spring and applies compressive force to the spring on squeeze of handle lever arms, and receives expansion force of the spring on release of handle lever arms. The front wall of foundation block has upper and lower guide posts 18k that ride between parallel axial rails 26d of the linear translator box described next below.

Main spring core 18m of linear translator extends axially rearward from foundation block rear wall for positioning the cylindrical main spring on the translator. The core presents a cylindrical surface defined by transverse discs and longitudinal ridges with recesses between discs and ridges. The front end coil 20a of the main spring abuts foundation block rear wall. The spring's back end coil 20b is squared off to abut translator shoulder 18n and retain spring on translator when the spring is slipped onto the translator and rotated 90°. The main spring back end coil abuts and is constrained by front face of rear wall 26b, and is compressed as the linear actuator is moved by squeeze of the handle lever arms. The main spring is also restrained by upper and lower longitudinal ribs 26d in the linear actuator box.

Anti-backup beam 18g of linear translator extends axially rearward from main spring core 18m, and under force of handle lever arms applied at cam oval slots 18d, moves through a linear excursion E between dash lines d and d' (FIG. 6). Beam 18g is defined by side walls connected by cross bars. Each side wall has two channel shaped notches 18p with beveled side faces aligned in pairs on lines d and d' for cooperating with anti-backup springs 36 as explained below. Beam side walls 18r have a drag surface along their outer side that is preferably smooth. The drag surface cooperates with anti-backup springs in a manner described below. As best shown in FIG. 6, the linear translator with beam is set into linear translator box with parallel axial rail support. As noted above upper and lower shell members are identical such that linear translator has upper and lower parallel rail support, with foundation block guide posts 18k sliding along between the rails 26d to maintain axial orientation of translator while it is in motion.

The linear translator further comprises cam oval slots 18d each defining a cam face 18s where handle lever arms apply force to move the linear translator axially rearward on a squeeze of handles, and where main spring force returns handles to normal (forward) position on release. Each cam oval is molded integral in linear translator and comprises base plate 18t and struts 18f joined to foundation block and to a side of cell 18b. Cam oval body is defined by an endless closed wall in the general shape of an oval with open interior space defining a cam surface along the inner run of oval body. Interior space and oval body each connect to handle lever arm by means of a cam pin 15b seen in FIGS. 2, 3, and 8. The cam surface may be divided functionally into a first lower force section 18s' and a second greater force section 18s". At the beginning of a squeeze of handle lever arms, cam pins exert a force of lower magnitude along the first section 18s', and as squeeze of handles continues the pins exert a greater force at the second section 18s". The handle squeeze applied through the oval cam surfaces continues movement of linear translator through a distance equal to excursion E (FIG. 6) while compressing the main spring to length C measured between box rear wall (line c) and position of block rear wall at the end of linear excursion (line c').

As shown in FIG. 6, a pair of anti-backup springs 36 occupy a rear section of handle housing with confronting spring tabs 36a engaging notches 18p on opposite sides of translator beam. The springs shown in FIGS. 2, 3, 6, and 8 include base 36c with spring fingers 36d, spring arm 36e extending from the base between spring fingers, and spring tabs 36a. Spring fingers are anchored in slots 12k formed in upper and lower housing members such that each spring arm is free to flex transversely of applier x-x' axis. Spring tabs 36a affixed to outer end of spring arms are held in "V" shape recesses 34 formed in the housing so as to position the free end of each tab for cooperation with beam notches. Each spring tab has upper and lower anchor posts 36b that register with cavities 34a formed in the housing shells. Anchor and cavity cooperation holds spring tabs square to the linear actuator beam 18g through the full range of actuator/spring cooperation. In this way the tabs perform a toggling action as the translator beam moves through a gap separating tab confronting edges. In toggling, each tab pivots slightly about its upper and lower anchor posts against the normalizing urging of spring arm. The spring arm urges its spring tab to position shown in FIG. 6.

When linear translator and anti-backup springs are assembled linear translator rear notches 18p reside in center gap defined by spring tab edges. The center gap provides an interference passage between confronting tab margins permitting the linear translator beam to pass through with tab margins dragging along smooth beam surfaces 18r. When handles and levers generate rearward linear movement of translator, translator beam moves through the slot and the tab edges drag along beam surface. In this dragging configuration, the tab edges prevent the linear translator moving in opposite, i.e., forward direction. If a surgeon releases the handles with tab edges in dragging configuration, handle main spring will not return handles to release position. So, it is necessary to resume rearward dragging movement of tab edges over beam surface until tab edges arrive at linear translator forward notches where they release beam surface and are able to toggle over so as to permit movement of linear actuator under influence of main spring in forward direction.

Referring now to FIGS. 9-24, clip cartridge 14 components comprise end cap 32, cartridge sleeve 50, cartridge chassis 52, cartridge cover 54, and cartridge interior operating components 56.

Figure 9:
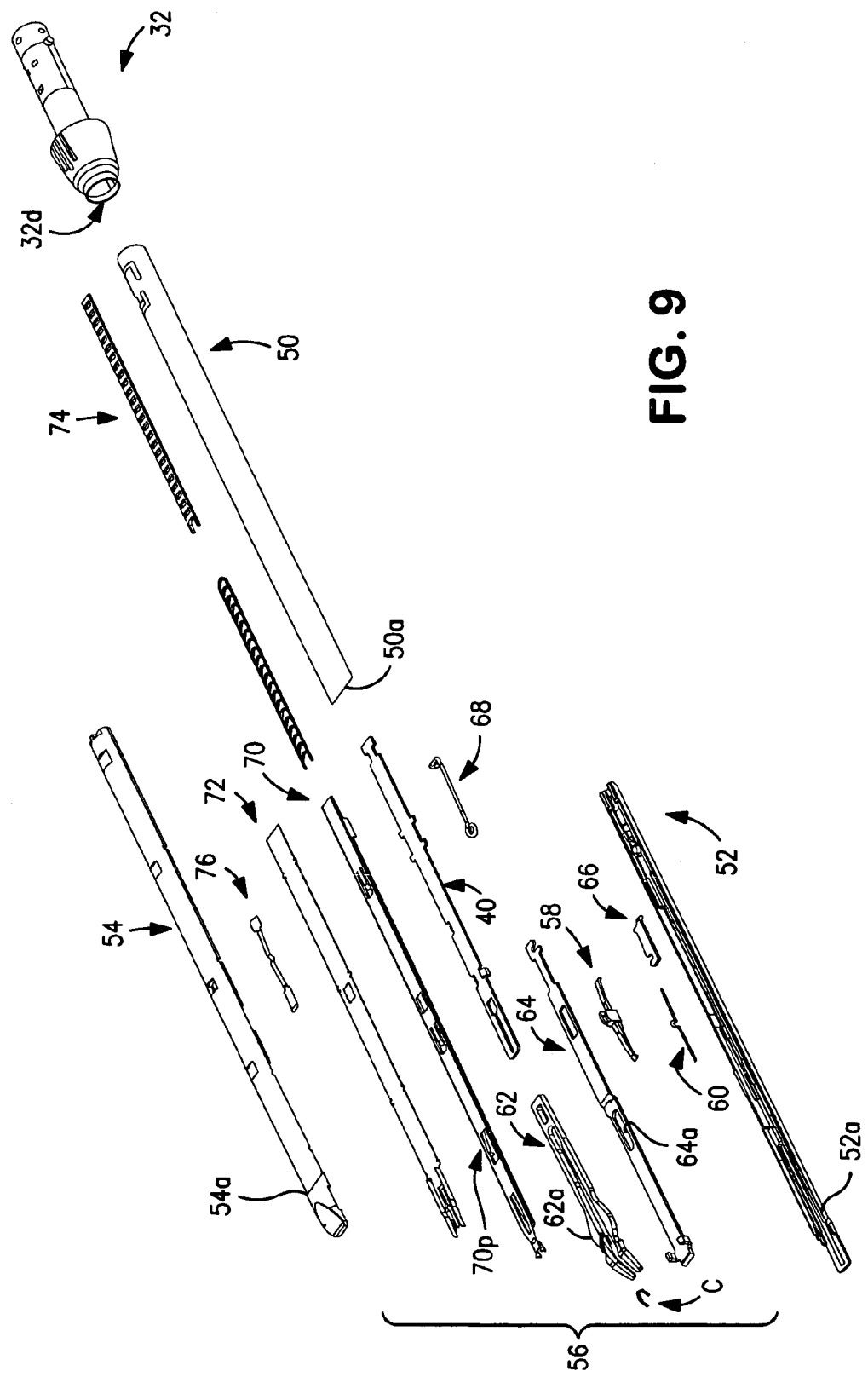
FIG. 9 is a perspective view layout of full complement of cartridge internal components including sleeve, chassis, cover, and first and second sets of cartridge members.
Figure 14:
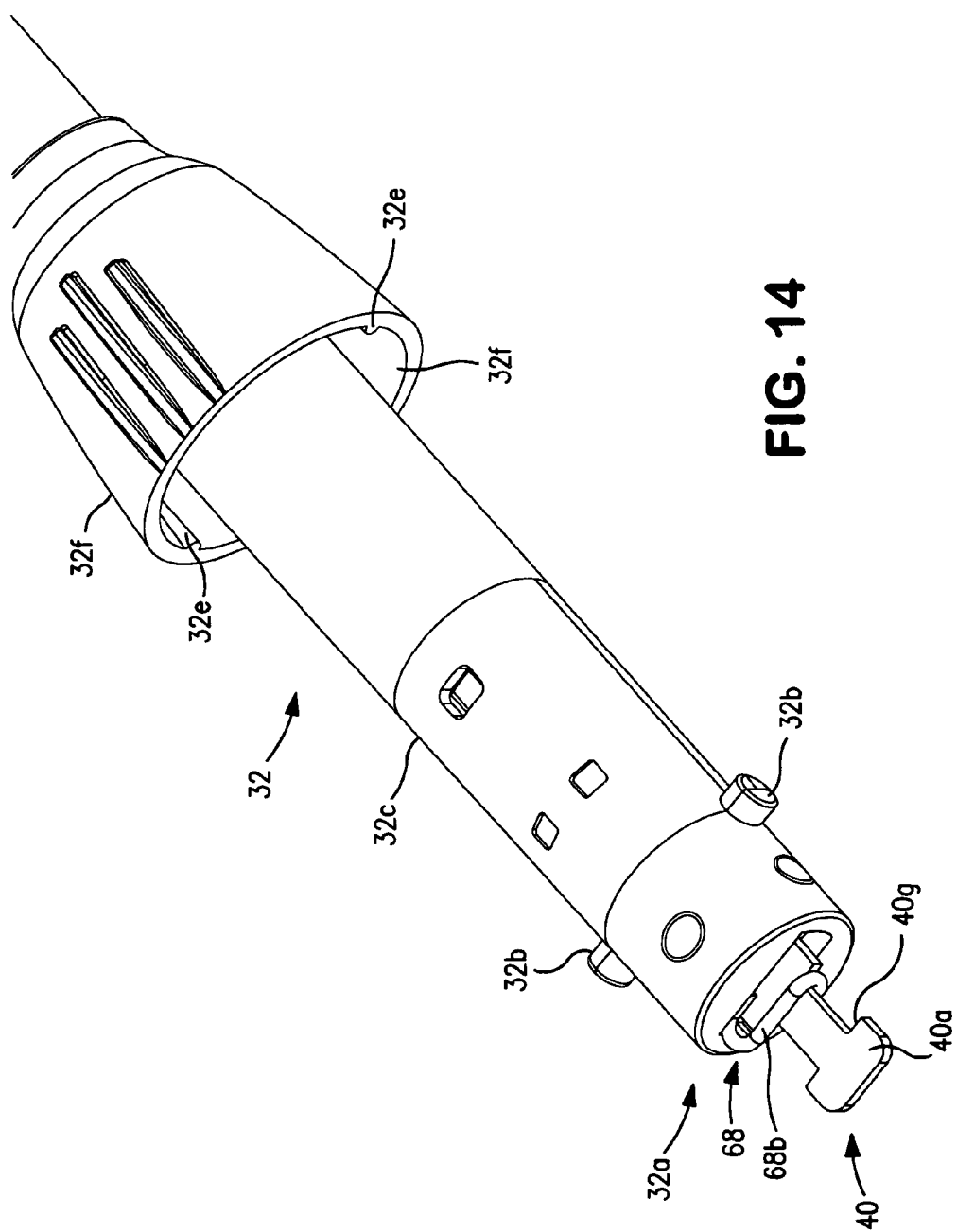
FIG. 14 is a perspective view of cartridge cap member showing position of cartridge puller bar T-end with puller lock.
Figure 15:
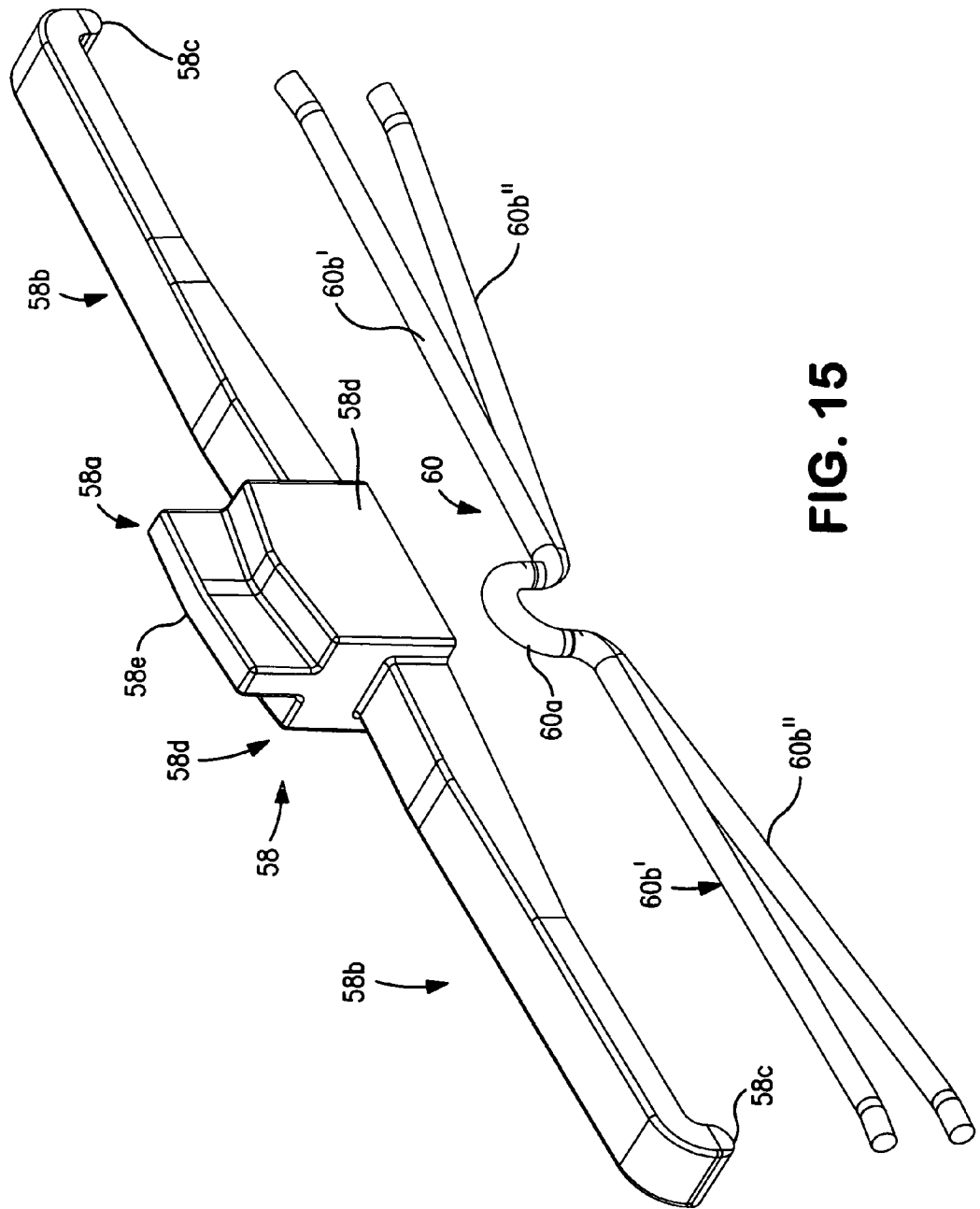
FIG. 15 is a perspective view cartridge lock out and spring.

Cartridge end cap 32 shown in FIGS. 9 and 14 as part of the clip cartridge assembly provides the means for interconnecting the cartridge to the handle. End cap comprises tubular body 32c with cylindrical axial cavity 32d for receiving cartridge sleeve in nested relation. A pair of positioning lugs 32b or posts project radially outward from opposite sides of body and lie in the same plane as the cartridge puller bar 40. This co-planar arrangement orients the T-end of the puller bar into necessary position for connection to handle linear actuator. When the end cap is assembled with the clip applier handle, positioning lugs enter socket channels 16m (FIG. 5) situated on the interior of upper and lower housing members, guide T-end toward and into apertured end wall 18h of linear translator cell 18b. The shaft cap is then rotated one-quarter turn clockwise for capturing the T-end within the cell and the positioning lugs 32b within transverse slots 16j provided in handle housing interior walls. It is by this connection that clip cartridge is held fast to the handle and that the handle transmits linear motion to the cartridge.

The shaft cap 32 is also retained rotationally by inner lugs 32e on the cap held by notches 16n (FIG. 5) situated at housing front face recess 16a. As shown in FIG. 14, the end cap has a conical cuff 32f over the front end of the cap, and within the cuff, diametrically opposed lugs 32e project inward from the cuff inner diameter. The cuff lugs engage diametrically opposed detent notches 16n at the handle front end as seen in FIGS. 4 and 5. It is observed in FIG. 14 that cap positioning lugs and cuff inner lugs 32b are co-planar. So as cartridge and handle are assembled and the cartridge is rotated one-quarter turn, the cuff lugs snap into place in the detent notches just as the cap positioning lugs enter transverse slots within the handle. The cuff lug and detent notch fit prevents inadvertent counter-rotation and resultant uncoupling of cartridge from handle.

FIG. 9 illustrates cartridge sleeve 50, cartridge chassis 52, cartridge cover 54, and cartridge interior operating components 56 in relative positions prior to being assembled into a functioning clip cartridge.

Figure 16:
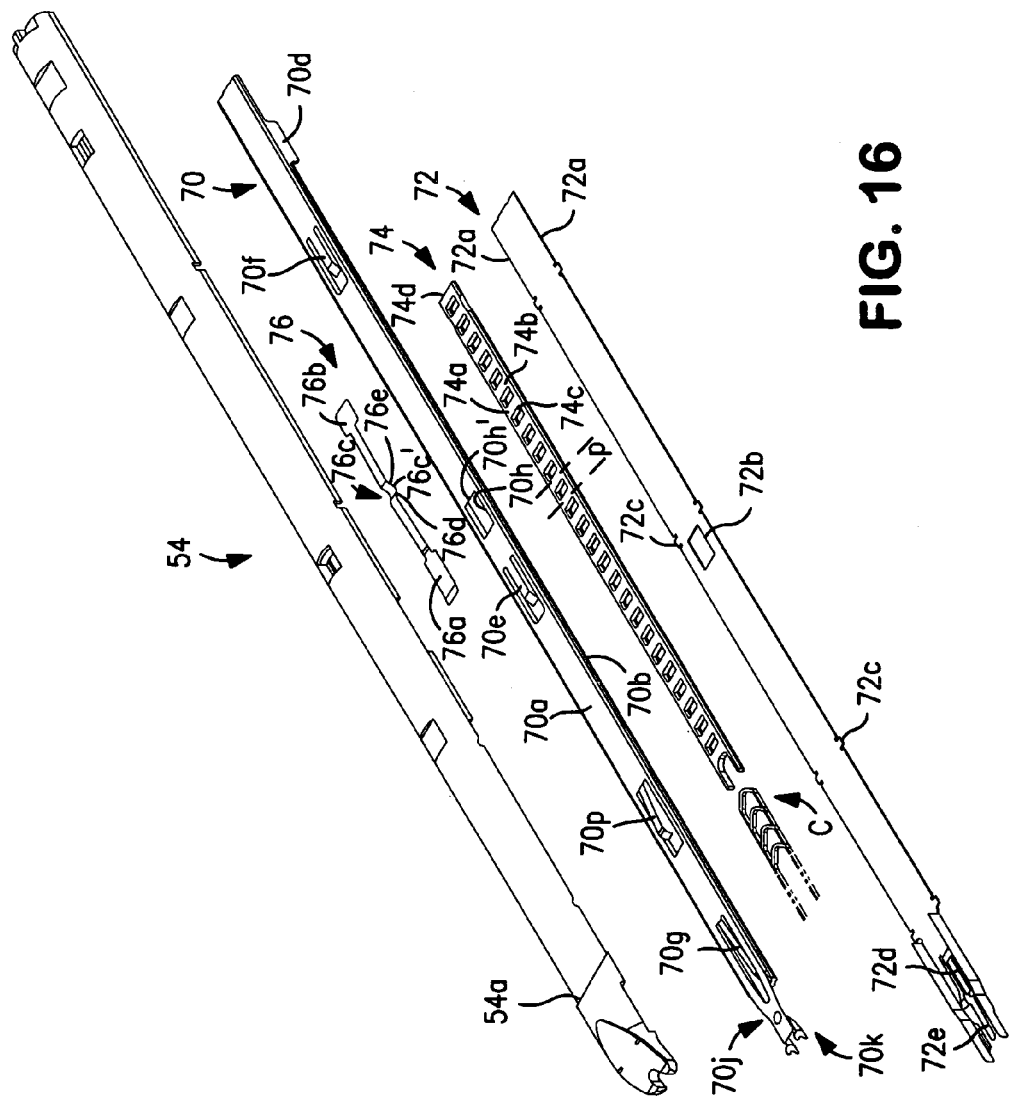
FIG. 16 is a perspective view of layout of second set of cartridge members that hold and advance surgical clips one-by-one into clip applicator jaws.
Figure 17:
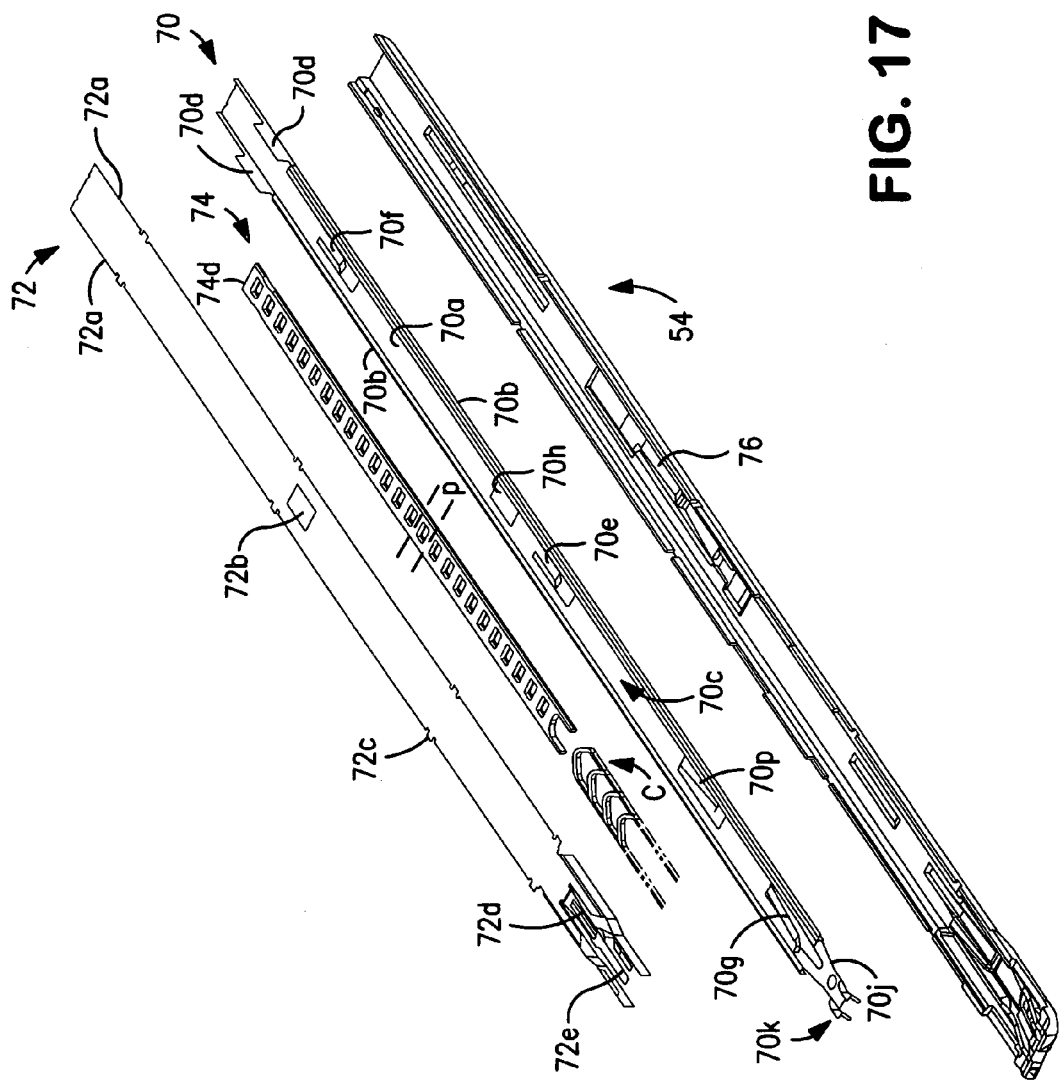
FIG. 17 is a perspective view of the underside of the cartridge members of FIG. 16.
Figure 18:
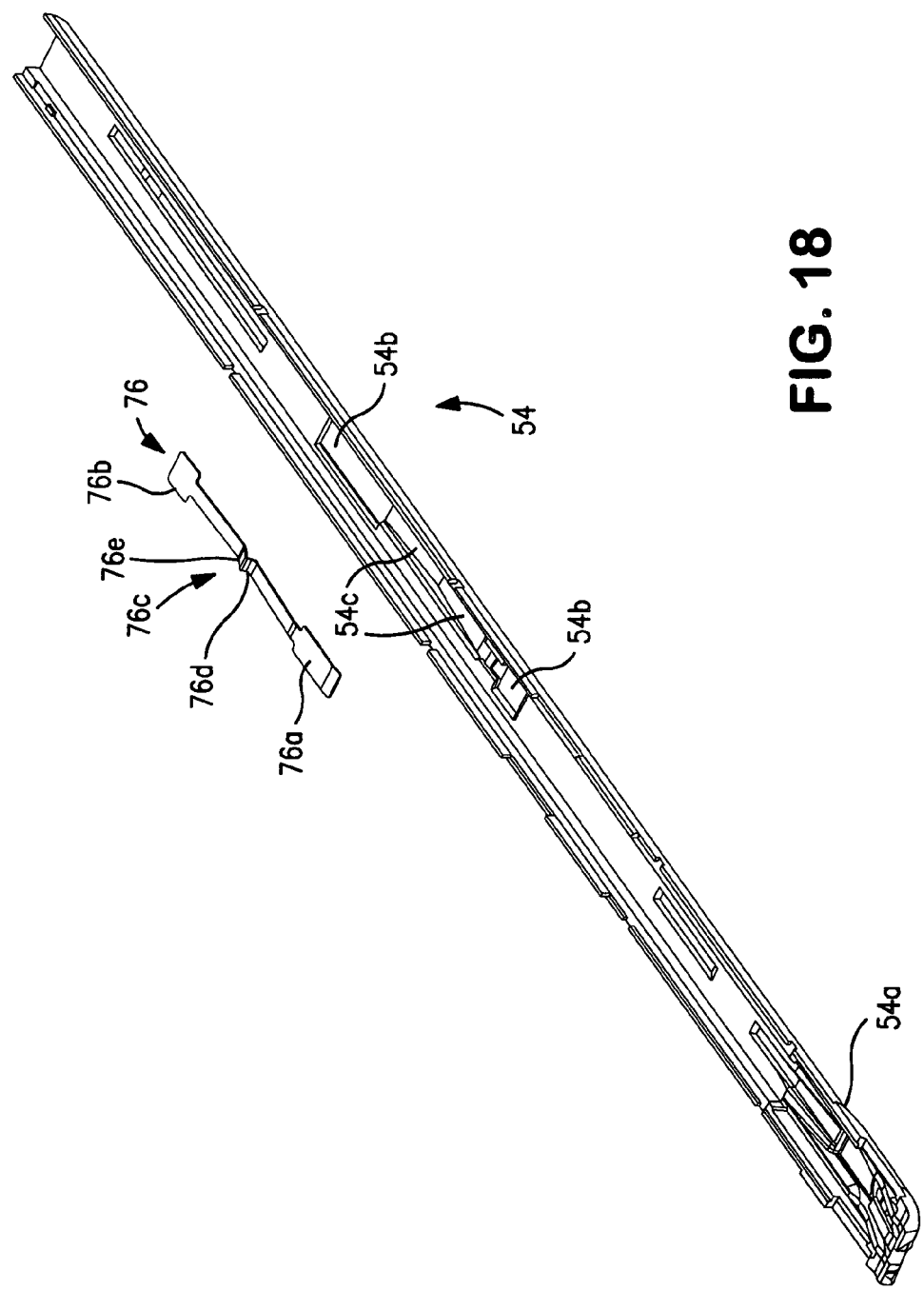
FIG. 18 is an articulated perspective of underside of cartridge cover and cartridge detent spring of FIG. 17.

The sleeve 50 is an elongate, preferably stainless steel, open-ended tube with bevelled front end 50a for abutment with cartridge chassis hips 52a and cartridge cover hips 54a shown in FIGS. 9 and 16.

Cartridge chassis 52 (FIG. 11) forms a stationary base with longitudinal channel 52b defined by base panel 52c with lock out recess 52d, upright side walls 52e, marginal edge notches 52f that fit corresponding cover edges, jaw post and cam bar guide post 52g, a front end opening 52h for clip applier jaws, a toggle cam surface 52j, post 52k for puller bar lock wire, and a puller bar rear end opening 52m with support ledge.

The lock out recess 52d opens through the base and has spaced ledges 52n including ledge panels and ledge end walls for supporting lock out block 58 and its spring 60.

The jaw end of the cartridge chassis is configured for mounting clip applying jaws 62 in normally open position allowing for the jaws to be cammed closed for applying surgical clip. Chassis sidewalls are recessed at 52p just aft of the front end opening for accommodating jaw apexes 62a with jaws in open position. As jaws open and close in operation, jaw apexes move in and out of sidewall recesses. The chassis base near its front end has upstanding oblong guide 52g with rounded ends that serves dual functions of jaw post and cam bar 64 guide as the bar reciprocates in operation. Accordingly, cam bar has oblong slot 64a for jaw post.

Components for actuation of the jaws and for locking the clip applier against actuation after the last clip is used, are mounted in stacked relation within the cartridge chassis. These components are jaws 62, jaws cam-bar 64, cam-bar safety toggle 66, puller bar 40, lockout 58, and puller bar lock rod 68 which is seen in FIGS. 9 and 14.

Lockout 58 comprises a central lug 58a with legs 58b of equal length extending away from the lug and terminating in downwardly depending tips 58c. The central lug side walls 58d are recessed and define narrow ridge 58e to accommodate reciprocating movement of puller bar as further described below. The combined length of the legs from tip to tip is approximately equal to the length between ends of ledges 52n in chassis recess 52d. The lock out fits into chassis recess with leg tips resting on ledges and abutting recess end walls. The lock out is provided with a spring 60 with a central node 60a for assembling lock out and spring, and spring arms 60b shown in stressed 60b' and unstressed 60b" positions.

Spring 60 gives biased flexing support for the central lug wherein the lug 58a is urged upward from chassis base panel to normal position, and the lug is readily pushed down against this spring action.

The chassis base panel has open chassis recesses that correspond to the legs of the lockout facilitating assembly of the lockout within cartridge. For ease of assembly, the openings allow the lockout to be inserted externally following assembly of other chassis components. Desired spring compression is achieved when cartridge sleeve 50 slides over cartridge chassis 52 and cover 54 and compresses the legs of the lockout creating the final spring loaded condition of the lockout.

Jaws 62 shown in FIGS. 12 and 13 comprise base plate 62b with jaw spring arms 62c extending in parallel from the base terminating in cooperating jaw heads 62d. The base plate has an opening 62e for securing the jaws to jaw post 52g of the cartridge chassis. The outer surfaces of each spring arm have cam surfaces 62f defined by triangular enlargements 62g extending along each arm behind its jaw head 62h.

A notch 62j intervenes between the rear surface of each jaw head and the beginning of each enlargement. So, cam surface 62f lies between the notch 62j and apex 62a of each jaw arm triangular enlargement for cooperation with cam-bar 64 that opens and closes the jaws by engaging cam surfaces with cam fingers 64b. The jaws have a natural spring bias to open position and are forced closed by cam-bar fingers for crimping a clip in surgery.

Jaws overlie cam bar 64 that receives linear reciprocating motion from cartridge puller bar 40 wherein cam bar fingers 64b open and close jaws as part of operating sequence of cartridge components. Cam bar finger tips 64b' are in-turned to overlie jaws top surface for keeping jaws and cam bar together as jaws are opened and closed. Jaw notches 62j overlap cam fingers and cooperate as shown in FIG. 13 to prevent occasional lateral flexing of the jaw arms that can occur when the jaws are tapped or dropped on a hard surface. Such lateral flexing of the jaws can partially deform (squeeze) a clip causing it to fall out of the jaws.

Jaws cam bar 64 shown in FIG. 12 comprises an elongate strip body with oblong slot 64a with rounded ends for fitting over chassis guide 52g. Oblong slot 64a accommodates chassis guide 52g by which jaws are secured by opening 62e to the chassis. Cam bar 64 further includes an oblong lock out slot 64c; a necked-down section 64d defined by recessed side edges 64d' extending between shoulders 64e by which the cam-bar receives reciprocating motion from the cartridge puller bar 40; and a toggle block 64f having interior sinuous toggle surface 64g for engagement and cooperation with cam-bar safety toggle 66.

Cam-bar safety toggle 66 shown in FIG. 12 is described in detail in Blake co-pending application Ser. No. 13/385,760 and comprises a plate with exterior sinuous toggle surface 66a for meshing with cam-bar interior sinuous toggle surface 64g for rotation about pivot point as cam-bar 64 is pulled by puller bar 40 in clip applier operation. The safety toggle is effective to nudge cam bar 64 forward after a clip is applied in surgery to prevent that condition where jaw cam surfaces 62f and cam bar fingers 64b adhere to each other and fail to separate after the jaws apply a clip.

The cam bar front end 64h (FIGS. 12, 13) defines a tissue fence to prevent tissue extending inward into jaws and pushing a clip backwards in the jaws as the applier is used in surgery.

Cartridge puller bar 40 comprises an elongate plate through which reciprocating motion developed by the clip applier handle is received by the cartridge and distributed to cartridge operating components both clip crimping jaws and surgical clip feeding mechanism by which clips are fed one by one into the clip crimping jaws for each cycle of the clip applier. The puller bar includes narrow 40b and wide 40c lockout slots for respectively accommodating upper ridge 58e of the lockout in narrow slot as the puller bar reciprocates over the lock out in normal operation, and accommodating the lockout body in wide slot as it rises to lock the clip applier from further operation after the last clip has been used in surgery. The puller bar further includes depending tangs 40d cooperating with cam-bar recesses 64d for moving the cam bar for closing the jaws in applying a clip in surgery and then releasing the jaws to receive another clip; a toggle tang 40e cooperating with cam bar safety toggle shoulder 66b for a purpose detailed below; edge shoulders 40f for accommodating magazine tangs through which the puller bar delivers reciprocating motion to the clip magazine components as more fully described below; and T-bar 40a connection to handle as described above.

Puller bar lock wire 68 (FIGS. 10 and 14) is a cartridge component for controlling position of the puller bar. Lock wire comprises an elongate rod with end coil 68a mounted over chassis post 52r, and an end loop 68b that nests in T-bar notch 40g to prevent puller bar from being pulled from cartridge before cartridge is assembled to clip applier handle. As the cartridge is inserted into handle and puller bar T-end enters translator cage and cartridge is rotated, a cam surface 12m (FIG. 4 in front of wall 26a) on the housing moves and keeps the lock wire loop out of the T-notch such that the puller bar can be moved by linear translator.

Figure 10:
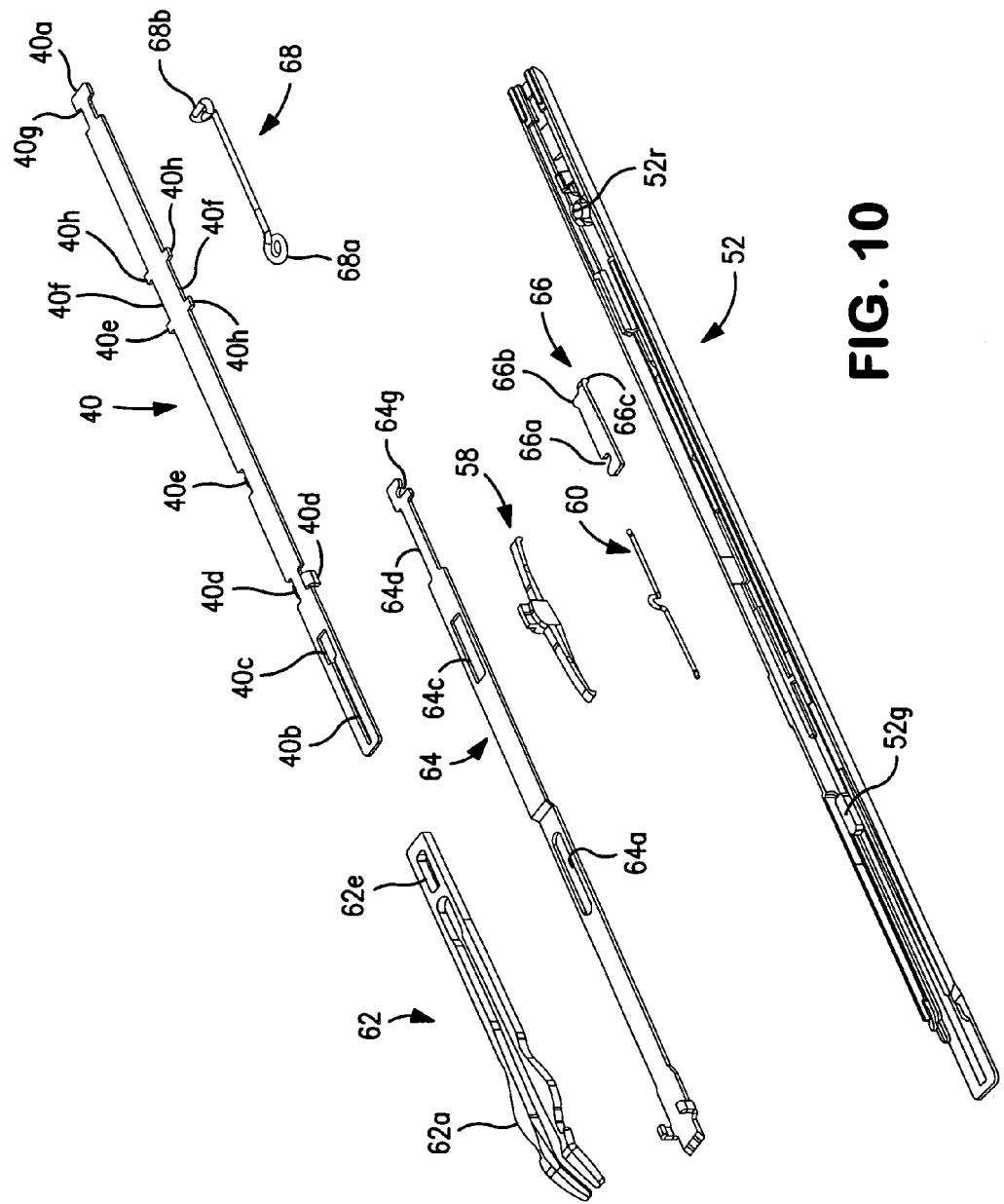
FIG. 10 is a perspective view of layout of first set of cartridge members that actuate clip applicator jaws.
Figure 11:
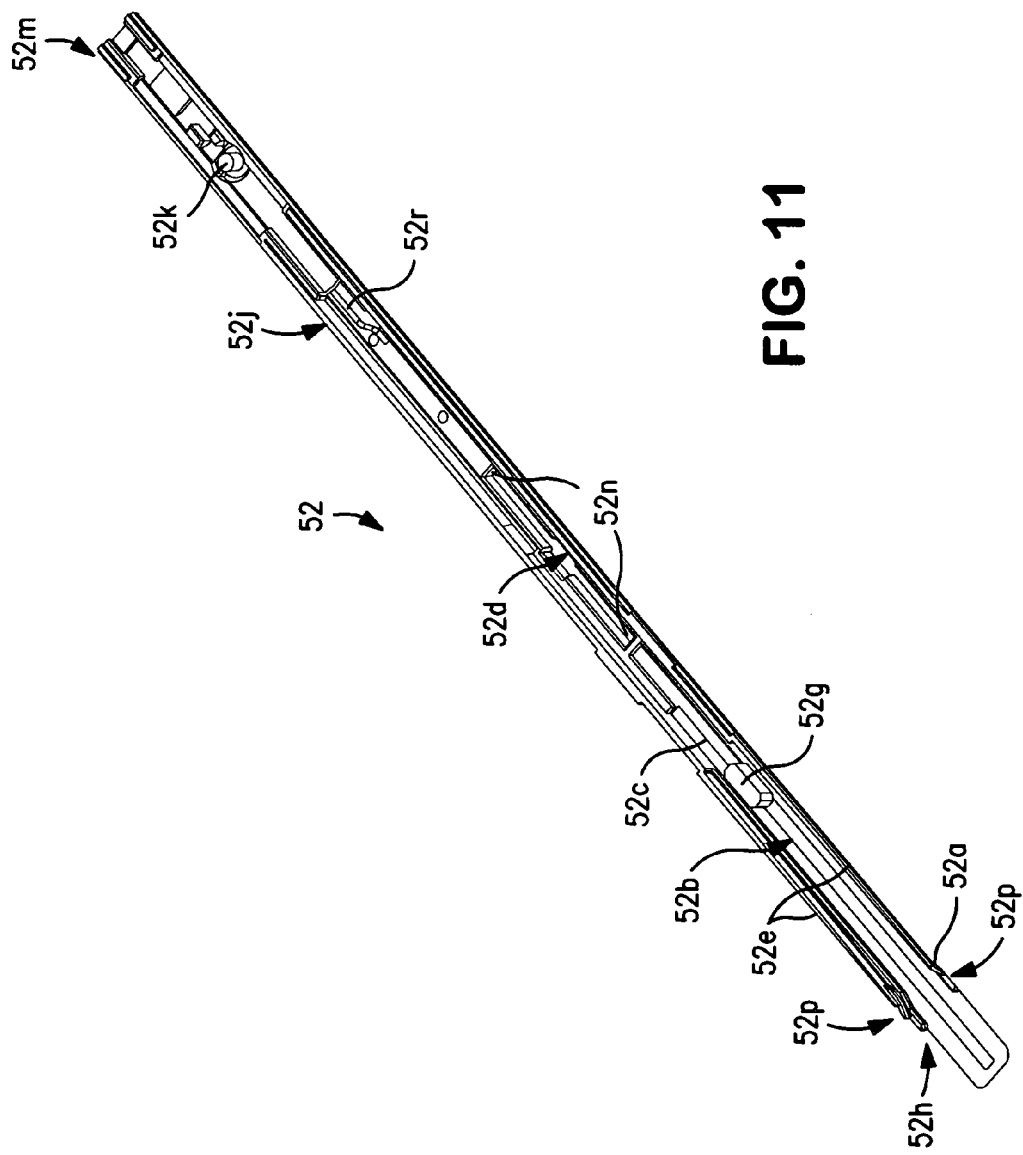
FIG. 11 is a perspective view of cartridge chassis member.

Referring to FIG. 10, jaws 62 are secured to chassis at jaw post 52g, and except for opening and closing, the jaws are stationary with respect to the chassis. Lockout 58 remains within its recess with its upwardly projecting block 58a being accommodated by cam bar opening 64c and puller bar narrow and wide slots 40b-c which pass over the lock out in normal operation of the clip applier. Cam bar lies between chassis and jaws with jaw post 52g passing through slot 64a, and the cam bar slot sliding past the post during applier operation.

Puller bar 40 overlies cam bar 64 and cam bar safety toggle 66 with puller bar lock out slots 40b-c aligned with lockout block 58, and tangs 40d in registry with cam bar recesses 64d.

Cam bar side edge recesses 64d cooperate with puller bar tangs 40d to create a hiatus in movement of jaws. The hiatus is an interval of jaws remaining open as a clip arrives and is being inserted into the jaws by clip handling mechanisms.

A clip is crimped by the handle moving the puller bar. As this motion is occurring, puller bar tangs 40d engage cam bar rear shoulders 64e' moving cam bar to the rear with cam bar jaw fingers 64b riding along cam surfaces 62f and closing the jaws. At the same time, cam bar safety toggle 66 pivots counterclockwise to locate shoulder 66b in the return path of puller bar tang 40e. The safety toggle is constrained to pivot about meshing sinuous surfaces 66a, 64g as its tang 66c rides in chassis cam track 52r (FIG. 11) to canted position.

When the handle is released handle main spring urges puller bar forward so that its tang 40e strikes shoulder 66b moving safety toggle 66 and cam bar 64 forward. Safety toggle tang rides down the chassis track 52r to normal position. Puller bar tang 40e comes to rest well forward of shoulder 66b in position for subsequent applicator cycle.

Puller bar edge recesses 40f and shoulders 40h deliver reciprocating motion to cartridge components now to be described for delivering clips one-by-one to the applicator jaws.

Components for holding and feeding surgical clips C one at a time to the applicator jaws are mounted in stacked relation within the cartridge. These components are clip magazine 70, magazine floor plate 72, clip stack C, clip advancing ladder 74, cover detent spring 76, and cartridge cover 54 as best seen in articulated over and underneath positions respectively in FIGS. 16 and 17. The cover detent spring 76 (FIG. 18) is mounted at recesses 54b in the underside of cover 54, the spring being stationary with respect to cyclical movements of clip magazine as described in detail below.

Clip magazine 70 is a C-shaped channel with main panel 70a and depending side panels 70b defining a cartridge chamber 70c or space for receiving and containing clip stack C aligned with clip advancing ladder 74. Clip magazine drive tangs 70d extend from marginal flanges for engagement with puller bar drive edges 40f and shoulders 40h. The tangs are point of reception of reciprocating motion generated by applier handles and used to actuate clip holding and feeding components. So, for each cycle of pull and return strokes of the clip applier handles, puller bar drives clip magazine with clip stack and clip advancing ladder through full reciprocating excursion generated by puller bar.

The clip stack (FIG. 24) comprises a line of clips C with clip tips Ca engaging shoulders Cs of clip next ahead. Accordingly, a clip increment Ci may be defined as the distance measured on a given clip between its tips and the point on the given clip's shoulders that is engaged by the tips of the next successive clip. Clip advancing ladder 74 is situated within the clip chamber 70c in longitudinal alignment with the clip stack C, and during operation of the clip applier ladder moves in unison with the clip stack. The stack and ladder along with the magazine 70 move toward and move away from the applier jaws.

The clip advancing ladder 74 comprises longitudinal, parallel beams 74a with rungs 74b spaced a clip increment Ci apart. An opening 74c exists in each space defined by beams and rungs for engagement with magazine detent springs 70e-f. The magazine detent springs each engage a ladder opening and hold the ladder and stack within magazine clip chamber as the full ensemble of magazine with detent springs, clips and ladder move toward the jaws. On return movement of the full ensemble, the magazine detent springs 70*d-e* slide past a single rung 74*b* as the ladder is restrained by stationary cover detent spring 76. The ladder may have recesses formed between rungs instead of illustrated openings 74*c*.

Clip magazine further comprises claw back spring 70*g* formed in main panel 70*a* for clawing back the clip stack C on the pull stroke of the handle that provides return travel of the clip magazine 70. For a portion of return travel of the clip magazine the cover detent spring 76 restrains movement of the ladder and clip stack so that magazine detent springs 70*e-f* ratchet over a rung 74*b* and come to rest in a rung opening 74*c* or recess closer to the end 74*d* of the ladder. So for a ladder rung pitch p equal to a clip increment Ci, the claw back spring 70*g* moves stack back, cover detent spring 76 holds ladder 74, and on forward magazine movement the ladder and stack move in unison so as to net one clip increment Ci forward movement for each pull and return cycle of the applier handle.

Clip magazine 70 further comprises rectangular slot 70*h* having dual functions, first, allowing cover detent spring 76 to extend through magazine panel to engage and restrain clip advancing ladder against rearward movement as the clip magazine is being returned by the puller bar, and second, as an opening for entry of lockout spring block 58 to inhibit cartridge movement after last clip is used in surgery. Normally, slot 70*g* is closed over by clip advancing ladder 74 as the ladder advances clip stack toward the jaws one at a time for each cycle of the clip applier. The trailing end 74*d* of the ladder moves past lock out slot 70*h* after the last clip is moved into the jaws, whereupon the lockout 58, being spring biased, rises and its central lug 58*a* enters and remains in slot 70*h*. The central lug also enters the puller bar lockout slot 40*c* (FIG. 10) to prevent further operation of the appliance. That is, movements of clip ladder and puller bar are, physically and permanently blocked, handles can no longer be actuated, and the clip applier is empty of clips and can no longer be used.

The cartridge cover 54 holds cover detent spring 76 in fixed longitudinal position above clip stack and clip advancing ladder, and provides cover recesses 54*c* to accommodate spring flexing. Cover detent spring 76 comprises elongate strip with end tabs 76*a-b* for cover mounting. The spring has a downwardly depending spring wall 76*c* defining an apex 76*c'*, stop face 76*d*, and a slide face 76*e*. In the forward rest position of the instrument with handles open and jaws open, apex 76*c'* rests on magazine surface to the right of slot 70*h* (FIG. 16). The spring wall enters magazine slot 70*h* as the magazine undergoes rearward (to the right in FIG. 16) movement on pull stroke of the handle. Spring stop face 76*d* situated in magazine slot engages a ladder opening 74*c* and stops further movement of the ladder. The dwell of spring stop face in magazine slot is regulated by magazine slot edge 70*h'*. As the magazine reverses movement on return stroke of the handles and moves toward the jaws, magazine slot edge 70*h'* engages slide face 76*e* of cover detent spring and lifts the spring wall out of magazine slot to ride along magazine wall surface. As a result of this intervention of the cover detent spring, ladder and line of clips slip one clip increment with respect to the clip magazine as spring stop face 76*d* engages a rung and stops ladder movement for each cycle of instrument handles.

While the stack and ladder are restrained by the cover spring, magazine detent springs 70*e*, 70*f* slide over stack and ladder and the operative spring (70*e* or 70*f* determined by remaining length of stack and ladder) slides over the ladder coming to rest in an opening closer to the rear of the ladder.

The clip magazine further comprises clip arm 70*j* and clip head 70*k* projecting from the front end of main panel for engaging a lead clip by its shoulder and pushing it into the jaws on each return stroke of applier handles.

Magazine floor plate 72 is mounted along the length of cartridge cover enclosing clip cartridge with clips and ladder within interior cover channel. Both cartridge cover and magazine floor plate are stationary during clip applier operation. Floor plate is an elongate strip with edges 72*a* situated within clip magazine drive tangs 70*d* that engage puller bar edge recesses 40*f* whereby puller bar delivers reciprocating motion to the clip magazine and its ladder and clip stack components; a lock out slot 72*b* accommodating the lock out 58 as it rises to lock the clip applier from further operation after the last clip has been used in surgery; edge recesses 72*c* engaging corresponding ridges on the cartridge cover for the purpose of holding the floor plate stationary to the cover against longitudinal movement; a clip capture spring 72*d* for separating a lead clip from the clip magazine preparatory to being moved into clip applying jaws; and front end ramps 72*e* for guiding a lead clip as it is being pushed into the jaws.

The cartridge cover is secured to the chassis and together with the chassis encases cartridge operating components. In addition, the cartridge cover cooperates with cartridge operation in the following aspects.

The clip applier cycle comprises a pull stroke and release stroke of the handle.

At start of the pull stroke as shown in FIG. 19 magazine floor plate capture spring 72*d* has moved into position behind lead clip C to hold it there for duration of the pull stroke. The components for moving clips are in forward position with clip Cj positioned in jaws. As pull begins and continues, clip magazine 70 being pulled back by the puller bar retreats from forward position, clip arm 70*j* and clip head 70*k* withdraw from jawed clip Cj, and pass between stationary floor plate ramps 72*e*. Claw back spring 70*g* engages cover cam surface 54*f* and moves downward to grasp next clip $C_n$ and pull line of clips backward. At the end of the pull stroke, clip head 70*k* rides over the captured clip C coming to a stop behind the clip's shoulder in preparation for pushing the clip on release stroke of the handle.

As the clip magazine moves to the rear on pull stroke, the cover detent spring 76 finds and enters magazine main panel opening 70*h* and restrains ladder movement so that the clip stack being drawn back by the claw spring closes up the space existing between stack and ladder. The cover detent spring is then lifted out of panel opening by slot edge 70*h'*. The ladder and line of clips therefore slip one clip increment along the clip magazine for each cycle of instrument handles.

On the return stroke of the applier handle (FIG. 20), the clip head 70*k* pushes captured clip over floor plate ramps 72*e* and beneath cover guide surface 54*g* into open jaws.

In order to ensure that the clip applier is capable of rapid fire operation without clip feeding failures it has been found necessary to control movement of the clip stack and pusher ladder mass at the conclusion of the return stroke of the applier so that stack and ladder do not overshoot their assigned position. To achieve such control of stack and ladder movement, a rapid fire pawl 70*p* shown in FIGS. 17, 21, 22, and 23*a-b* is made part of the clip magazine. Pawl is formed in magazine main panel and comprises an elongate spring strip with first transverse bend line 70*r* by which spring strip projects above main panel surface, and a second transverse bend 70*s* line defining tab 70*t*. It is tab 70*t* that engages and controls stack and ladder movement in rapid fire operation of the clip applier.

Figure 21:
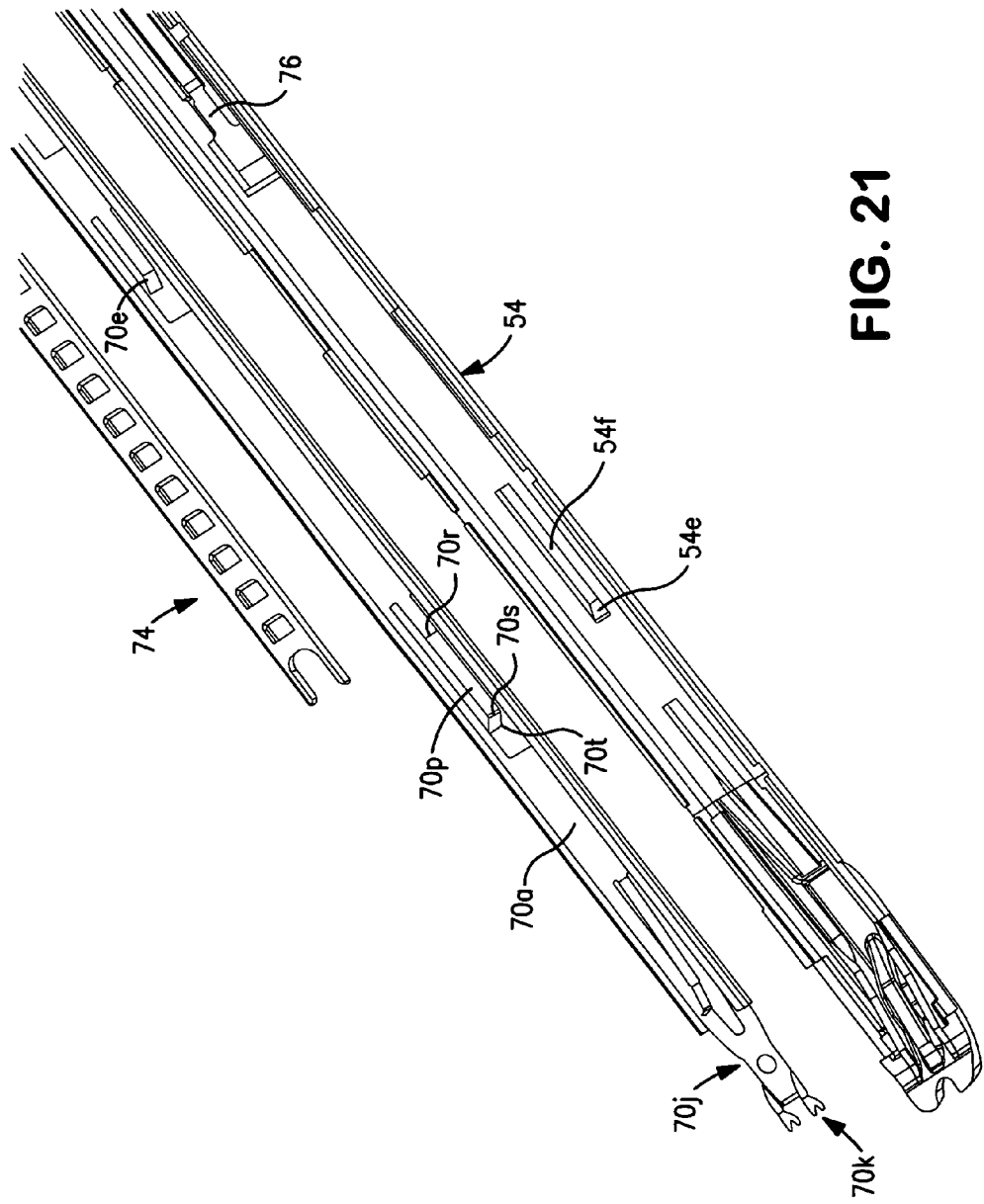
FIG. 21 is a fragmentary perspective view of the underside of the cartridge members of FIG. 17 showing rapid fire pawl and ramp camming surface.

The clip applier cover 54 is recessed 54f to accommodate the rapid fire pawl. As shown in FIGS. 21 and 22, cover recess is generally rectangular to receive the spring strip configuration of the pawl, and further has an inclined cam surface or ramp 54e for engaging and pushing the pawl tab 70t below magazine main panel 70a and into the path of the pusher coming to rest in a pusher slot thus constraining clip stack and pusher ladder to assigned position at the end of the return stroke of the clip applier.

At rest the rapid fire pawl is bent outward from the pathway of the clip stack and pusher ladder moving linearly through the magazine. In assembly the pawl is located in its cover slot. On the return stroke, the pawl maintains such bent outward configuration for a prescribed distance at which, the tab 70t of the pawl reaches the ramp 54e and is cammed upward to positively engage the pusher ladder thereby arresting its relative forward movement and absorbing the force creating a clip feed disruption. Interception of the stack and ladder by the rapid fire pawl occurs near the end of the return stroke thereby preventing follow-through inertia of the combined mass from exceeding the mark and disrupting clip feed.

Various changes may be made to the structure embodying the principles of the invention. The foregoing embodiments are set forth in an illustrative and not in a limiting sense. The scope of the invention is defined by the claims appended hereto.

We claim:

1. An operating handle providing for linear reciprocating movement to an instrument cartridge having means for receiving said movement, the handle having an axis and comprising a housing, the housing defining a socket for receiving and holding the cartridge in the handle, handle lever arms for initiating reciprocating movement, a linear translator mounted within the housing for generating linear reciprocating motion of fixed excursion, the linear translator connected to said cartridge whereby said motion is transmitted to the cartridge, the linear translator having twin cam oval bodies, each cam oval body defined by an endless closed wall with open interior space defining a cam slot, each handle lever arm having a cam pin connected to the cam slot of one of the twin cam oval bodies through which said handle lever arms move said linear translator along said axis, the linear translator having an anti-backup beam, a main spring mounted on the anti-backup beam for urging the linear translator to a normal position in which the handle lever arms are in a release operating condition, anti-backup springs cooperating with the anti-backup beam for limiting handle lever arm movement to full pull and release strokes whereby manually squeezing the handle lever arms draws the linear translator through linear motion of fixed excursion against a main spring force, and by release of the lever arms, the main spring force urges the linear translator in a return motion of fixed excursion to the normal position.

2. An operating handle as defined in claim 1 in which the socket has a back wall, the linear translator comprises a cell for receiving and retaining the cartridge movement receiving means, the cell engaging the back wall to limit excursion of said linear translator on said return motion, and an anti-backup beam for positioning said main spring and for cooperating with said anti-backup springs for limiting handle movement to full pull and release strokes.

3. An operating handle as defined in claim 1 in which the cartridge movement receiving means is a puller bar with a T-shaped end, and further in which the linear translator comprises a cell for receiving and retaining the T-shaped end, a foundation block for supporting said cam oval bodies, for bearing force of said handle lever arms on said cam slots, and for bearing force of the main spring, and a main spring core between said foundation block and said anti-backup beam for centering said main spring on the linear translator.

4. An operating handle as defined in claim 1 in which each cam slot is divided into a first lower force section and a second greater force section wherein at the beginning of a squeeze of handle lever arms, the cam pins exert a force of lower magnitude along the first section, and as the squeeze of handle lever arms continues, the cam pins exert a greater force at the second section.

5. An operating handle as defined in claim 4 in which the squeeze of handle lever arms continues movement of the linear translator through a distance equal to a fixed excursion while compressing the main spring.

6. An operating handle as defined in claim 1 in which the anti-backup beam is defined by side walls, each side wall having two notches aligned in pairs for cooperating with said anti-backup springs, each side wall having a drag surface along an outer side thereof.

7. An operating handle as defined in claim 1 in which the housing defines a linear translator box with a parallel axial rail support, said linear translator being set into the box, and the linear translator having a foundation block with guide posts adapted to slide along the the parallel axial rail support to maintain axial orientation of said linear translator while said linear translator is in motion.

8. An operating handle as defined in claim 1 in which the linear translator has a foundation block and a transverse shoulder, the main spring having a front end coil and a back end coil, the front end coil engaging the foundation block, the back end coil is squared off to abut said transverse shoulder and retain the main spring on said linear translator when the main spring is slipped onto the linear translator and rotated 90°.

9. An operating handle as defined in claim 1 in which each anti-backup spring comprises a base, spring fingers, a spring arm extending from the base between spring fingers, and a spring tab, wherein each spring tab has an edge in confronting relation to each other for cooperation with the anti-backup beam.

10. An operating handle as defined in claim 9 in which said confronting spring tabs engage front and rear notches and drag surfaces on opposite sides of said anti-backup beam.

11. An operating handle as defined in claim 9 further having slots formed in upper and lower housing members in which the spring fingers are anchored such that each spring arm is free to flex transversely of said axis.

12. An operating handle as defined in claim 10 further having "V" shape recesses formed in the housing in which said spring tabs are held in so as to position the edge of each spring tab for cooperation with said front and rear notches.

13. An operating handle as defined in claim 10 wherein cavities are formed within the housing and each spring tab has upper and lower anchor posts that register with the cavities to anchor and hold said spring tabs square to the anti-backup beam for full pull and release strokes of the handle lever arms.

14. An operating handle as defined in claim 10 in which said linear translator and said anti-backup springs are assembled with the rear notches residing in a center gap defined by the spring tab edges, the center gap providing an interference passage permitting the anti-backup beam to pass through with tab margins dragging along said drag surfaces when said handle lever arms generate rearward linear movement of said linear translator so that the spring tab edges prevent the linear translator from moving in an opposite direction whereby release of the handle lever arms with the spring tab edges in a dragging configuration, the main spring does not return the handle lever arms to the release position, whereby it is necessary to resume rearward dragging movement of the spring tab edges over said drag surfaces until the spring tab edges arrive at the forward notches where the forward notches release said drag surfaces and toggle over to permit movement of the linear translator under influence of the main spring in a forward direction.

* * * * *